US012045982B2

(12) United States Patent
Chen et al.

(10) Patent No.: US 12,045,982 B2
(45) Date of Patent: Jul. 23, 2024

(54) PREDICTING CELLULAR PLURIPOTENCY USING CONTRAST IMAGES

(71) Applicant: Insitro, Inc., South San Francisco, CA (US)

(72) Inventors: Matthew Chen, Palo Alto, CA (US); Lauren Schiff, San Mateo, CA (US); Alicia Cuevas, San Leandro, CA (US); Kelly Haston, Pacifica, CA (US); Haoyang Zeng, Redwood City, CA (US); Cody Scandore, San Diego, CA (US)

(73) Assignee: INSITRO, INC., South San Francisco, CA (US)

( * ) Notice: Subject to any disclaimer, the term of this patent is extended or adjusted under 35 U.S.C. 154(b) by 0 days.

(21) Appl. No.: 18/233,275

(22) Filed: Aug. 11, 2023

(65) Prior Publication Data
US 2023/0401704 A1    Dec. 14, 2023

Related U.S. Application Data

(63) Continuation of application No. PCT/US2022/032716, filed on Jun. 8, 2022.
(Continued)

(51) Int. Cl.
*G06T 7/00* (2017.01)
*G06V 10/82* (2022.01)
*G06V 20/69* (2022.01)

(52) U.S. Cl.
CPC ............ *G06T 7/0012* (2013.01); *G06V 10/82* (2022.01); *G06V 20/695* (2022.01); *G06T 2207/10056* (2013.01); *G06T 2207/10064* (2013.01); *G06T 2207/20084* (2013.01); *G06T 2207/30072* (2013.01); *G06V 2201/04* (2022.01)

(58) Field of Classification Search
None
See application file for complete search history.

(56) References Cited

U.S. PATENT DOCUMENTS

2020/0224172 A1*   7/2020   Schiebinger ........... C12N 15/86
2020/0320394 A1*  10/2020   Nelson .................... G06N 3/045

FOREIGN PATENT DOCUMENTS

WO     2016/138289 A1    9/2016

OTHER PUBLICATIONS

Kusumoto, Dai, et al. "Automated deep learning-based system to identify endothelial cells derived from induced pluripotent stem cells." Stem cell reports 10.6 (2018): 1687-1695. (Year: 2018).*

(Continued)

*Primary Examiner* — Samah A Beg
(74) *Attorney, Agent, or Firm* — Goodwin Procter LLP

(57) ABSTRACT

Embodiments of the disclosure include methods for implementing a predictive model that predicts pluripotency of cells through a cost efficient and non-destructive means. The predictive model analyzes contrast images captured from the cells and outputs predictions of cellular pluripotency at the cellular level. Thus, implementation of the predictive model guides the selection and isolation of cells that are predicted to be pluripotent. Furthermore, the predictive model facilitates retrospective analyses to correlate pluripotency metrics with differentiation success and further enables tracking of cellular pluripotency over time (e.g., to evaluate differentiation of cells).

24 Claims, 10 Drawing Sheets

Related U.S. Application Data

(60) Provisional application No. 63/208,287, filed on Jun. 8, 2021.

(56) References Cited

OTHER PUBLICATIONS

Ben-David, Uri, and Nissim Benvenisty. "Chemical ablation of tumor-initiating human pluripotent stem cells." nature protocols 9.3 (2014): 729-740. (Year: 2014).*

Waisman, Ariel, et al. "Deep learning neural networks highly predict very early onset of pluripotent stem cell differentiation." Stem cell reports 12.4 (2019): 845-859. (Year: 2019).*

Long, Jonathan, Evan Shelhamer, and Trevor Darrell. "Fully convolutional networks for semantic segmentation." Proceedings of the IEEE conference on computer vision and pattern recognition. 2015. (Year: 2015).*

International Search Report and Written Opinion for PCT/US22/32716, mailed on Sep. 6, 2022, 8 pages.

Hernandez, C., et al., "Using Deep Learning for Segmentation and Counting within Microscopy Data", Feb. 28, 2018, arXiv: 1802.10548v1.

Araujo, F., et al., "Deep learning for cell image segmentation and ranking", Comput Med Imaging Graph. 2019; 72: pp. 13-21.

Stringer, C., "Cellpose: a generalist algorithm for cellular segmentation", Nat Methods 18, 100-106 (2021).

Buxbaum, A., et al., "Single b-Actin mRNA Detection in Neurons Reveals a Mechanism for Regulating Its Translatability", Science 343, 419-422 (2014).

Eng, Ch.L., et al., "Transcriptome-scale super-resolved imaging in tissues by RNA seqFISH+". Nature 568, 235-239 (2019).

Hu, L., et al., "A molecular pathology method for sequential fluorescence in situ hybridization for multi-gene analysis at the single-cell level", Oncotarget 8(31): 50534-50541 (2017).

* cited by examiner

PREDICTING CELLULAR PLURIPOTENCY USING CONTRAST IMAGES

CROSS-REFERENCE TO RELATED APPLICATIONS

This application is a bypass continuation of PCT/US2022/032716, filed Jun. 8, 2022, which claims the benefit of and priority to U.S. Provisional Patent Application No. 63/208,287 filed Jun. 8, 2021, the entire disclosure of which is hereby incorporated by reference in its entirety for all purposes.

BACKGROUND OF THE INVENTION

Current methods for characterizing pluripotency of cells involve destructive means. For example, a cell sample needs to undergo fixing and staining protocols to identify presence or absence of markers that are indicative of cellular pluripotency. However, after the analysis, cells are no longer viable and therefore, pluripotent cells cannot be further used for subsequent experimentation. Thus, there is a need for a cost efficient and non-destructive means for determining pluripotency of cells.

SUMMARY

Disclosed herein are methods for implementing a predictive model that predicts pluripotency of cells through non-destructive means. In various embodiments, predictive models disclosed herein learn a transformation from contrast images to an intermediate mask representation. For example, the intermediate mask representation can represent known pluripotency markers, such as an immunofluorescent biomarker (e.g., Nanog, Oct4, Sox2, or others that correspond to cellular pluripotency) or can represent sequencing data (e.g., DNA or RNA sequencing) that is known to correspond to cellular pluripotency. Thus, a predictive model analyzes contrast images captured of cells and predicts pluripotency of individual cells in the contrast image. Additionally, a predictive model determines spatial localization of cells within the contrast image. Altogether, the predictive model can be implemented to determine pluripotency at the cellular level, thereby guiding selecting and isolation of individual cells for further analysis. Furthermore, the predictive model facilitates retrospective analyses for correlating pluripotency metrics with differentiation success and further enables tracking of cellular pluripotency over time (e.g., to evaluate differentiation potential of cells).

Disclosed herein is a method for characterizing pluripotency of a plurality of cells, the method comprising: obtaining a contrast image of the plurality of cells; applying a predictive model to the contrast image, the predictive model configured to translate the contrast image to an intermediate mask representation indicative of pluripotency of the plurality of cells in the contrast image; and generating pluripotency metrics for the plurality of cells according to the intermediate mask representation, the pluripotency metrics indicative of pluripotency of the plurality of cells.

In various embodiments, the intermediate mask representation is an intensity mask comprising pluripotency predictions of biomarker intensities for the plurality of cells. In various embodiments, the biomarker intensities comprise intensities of biomarkers selected from any of Oct4, Sox2, Klf4, c-Myc, Nanog, Lin28, SSEA-4, Tra-1-60, Tra-1-81, Alkaline Phosphatase, CD9, E-cadherin, and PODXL. In various embodiments, the pluripotency biomarker intensities are immunofluorescence intensities. In various embodiments, the intermediate mask representation is an intensity mask comprising pluripotency predictions of transcriptional profiles of one or more genes correlated to cellular pluripotency. In various embodiments, the transcriptional profiles of one or more genes correlated to cellular pluripotency represent transcriptional profiles determined via RNA fluorescent in situ hybridization (RNA-FISH) or sequential fluorescence in situ hybridization (SeqFISH+).

In various embodiments, the intermediate mask representation is a representation comprising pluripotency predictions according to sequencing data. In various embodiments, the sequencing data comprise RNA-seq sequencing data describing transcriptional sequencing profiles that are indicative of pluripotency. In various embodiments, the sequencing data comprise DNA-seq sequencing data. In various embodiments, the DNA-seq sequencing data comprise ATACseq sequencing data. In various embodiments, the sequencing data comprise epigenetic signatures that are indicative of pluripotency. In various embodiments, the epigenetic signatures comprise histone or DNA methylation statuses of a genome that are indicative of pluripotency. In various embodiments, the intermediate mask representation shares a same image resolution as the contrast image.

In various embodiments, the predictive model is a neural network. In various embodiments, the predictive model is a convolutional neural network comprising downsampling operators and upsampling operators. In various embodiments, applying the predictive model further comprises applying a cell localization model to the contrast image, the cell localization model configured to identify locations of the plurality of cells within the contrast image. In various embodiments, the cell localization predictive model generates bounding box localizations for each cell of at least a subset of the plurality of cells. In various embodiments, generating pluripotency metrics for the plurality of cells further comprises using the identified locations of the plurality of cells predicted by the cell localization model. In various embodiments, generating pluripotency metrics for the plurality of cells further comprises: for a cell at an identified location predicted by the cell localization model: determining a proportion of pixels in the intermediate mask representation at the identified location with a value that is indicative of the cell being pluripotent. In various embodiments, generating pluripotency metrics for the plurality of cells further comprises: for a cell at an identified location predicted by the cell localization model: transforming pixels of the intermediate mask representation at the identified location into binary values of a binary image; and determining a proportion of pixels at the identified location with a binary value that is indicative of the cell being pluripotent. In various embodiments, the binary value indicative of the cell being pluripotent exceeds a threshold intensity value.

In various embodiments, generating pluripotency metrics for the plurality of cells comprises generating a pluripotency metric for each cell of the plurality of cells. In various embodiments, methods disclosed herein further comprise identifying one or more cells from the plurality of cells based on the generated pluripotency metrics, the identified one or more cells having pluripotency metrics indicating higher probability of pluripotency in comparison to non-identified cells. In various embodiments, methods disclosed herein further comprise isolating the identified one or more cells from the plurality of cells. In various embodiments, isolating the one or more cells comprises ablating non-identified cells while maintaining the identified one or more cells. In various embodiments, isolating the one or more cells comprises: physically removing the isolated one or more cells from the plurality of cells; and culturing the physically removed isolated one or more cells.

In various embodiments, the predictive model is trained with paired contrast images and immunofluorescent images. In various embodiments, the predictive model is trained with paired contrast images and sequencing data. In various embodiments, obtaining the contrast image of the plurality of cells comprises: culturing the plurality of cells; and capturing the contrast image of the plurality of cells. In various embodiments, obtaining the contrast image of the plurality of cells comprises receiving the contrast image of the plurality of cells. In various embodiments, the plurality of cells are cultured in vitro or ex vivo. In various embodiments, the plurality of cells are selected from any of induced pluripotent cells (iPSCs), embryonic stem cells, or cells derived from germ layers. In various embodiments, the plurality of cells are selected from any one of cells derived from an ectoderm layer, cells derived from a mesoderm layer, cells derived from an endoderm layer, embryonic stem cells, terminally differentiated cells, or pluripotent cells.

In various embodiments, methods disclosed herein further comprise generating a second set of pluripotency metrics for the plurality of cells; and determining changes in pluripotency in the plurality of cells using the generated pluripotency metrics and the second set of pluripotency metrics. In various embodiments, methods disclosed herein further comprise subsequent to generating pluripotency metrics for the plurality of cells and prior to generating the second set of pluripotency metrics for the plurality of cells, providing a treatment to the plurality of cells, wherein the determined changes in pluripotency is dependent at least in part on the provided treatment to the plurality of cells.

In various embodiments, the contrast image is any of a bright-field image, phase-contrast image, dark-field image, Reinberg Illumination image, or polarization image. In various embodiments, the contrast image is captured using optical microscopy. In various embodiments, the predictive model achieves an accuracy of at least 0.90. In various embodiments, the predictive model achieves a precision of at least 0.90. In various embodiments, the predictive model achieves a recall of at least 0.75.

Additionally disclosed herein is a non-transitory computer readable medium for characterizing pluripotency of a plurality of cells, the non-transitory computer readable medium comprising instructions that, when executed by a processor, cause the processor to: obtain a contrast image of the plurality of cells; apply a predictive model to the contrast image, the predictive model configured to translate the contrast image to an intermediate mask representation indicative of pluripotency of the plurality of cells in the contrast image; and generate pluripotency metrics for the plurality of cells according to the intermediate mask representation, the pluripotency metrics indicative of pluripotency of the plurality of cells. In various embodiments, the intermediate mask representation is an intensity mask comprising pluripotency predictions of biomarker intensities for the plurality of cells. In various embodiments, the biomarker intensities comprise intensities of biomarkers selected from any of Oct4, Sox2, Klf4, c-Myc, Nanog, Lin28, SSEA-4, Tra-1-60, Tra-1-81, Alkaline Phosphatase, CD9, E-cadherin, and PODXL. In various embodiments, the pluripotency biomarker intensities are immunofluorescence intensities. In various embodiments, the intermediate mask representation is an intensity mask comprising pluripotency predictions of transcriptional profiles of one or more genes correlated to cellular pluripotency. In various embodiments, the transcriptional profiles of one or more genes correlated to cellular pluripotency represent transcriptional profiles determined via RNA fluorescent in situ hybridization (RNA-FISH) or sequential fluorescence in situ hybridization (SeqFISH+).

In various embodiments, the intermediate mask representation is a representation comprising pluripotency predictions according to sequencing data. In various embodiments, the sequencing data comprise RNA-seq sequencing data describing transcriptional sequencing profiles that are indicative of pluripotency. In various embodiments, the sequencing data comprise DNA-seq sequencing data. In various embodiments, the DNA-seq sequencing data comprise ATACseq sequencing data. In various embodiments, the sequencing data comprise epigenetic signatures that are indicative of pluripotency. In various embodiments, the epigenetic signatures comprise histone or DNA methylation statuses of a genome that are indicative of pluripotency.

In various embodiments, the intermediate mask representation shares a same image resolution as the contrast image. In various embodiments, the predictive model is a neural network. In various embodiments, the predictive model is a convolutional neural network comprising downsampling operators and upsampling operators.

In various embodiments, the instructions that cause the processor to apply the predictive model further comprises instructions that, when executed by the processor, cause the processor to apply a cell localization model to the contrast image, the cell localization model configured to identify locations of the plurality of cells within the contrast image. In various embodiments, the cell localization predictive model generates bounding box localizations for each cell of at least a subset of the plurality of cells. In various embodiments, the instructions that cause the processor to generate pluripotency metrics for the plurality of cells further comprise instructions that, when executed by the processor, cause the processor to use the identified locations of the plurality of cells predicted by the cell localization model. In various embodiments, the instructions that cause the processor to generate pluripotency metrics for the plurality of cells further comprise instructions that, when executed by the processor, cause the processor to: for a cell at an identified location predicted by the cell localization model: determine a proportion of pixels in the intermediate mask representation at the identified location with a value that is indicative of the cell being pluripotent. In various embodiments, the instructions that cause the processor to generate pluripotency metrics for the plurality of cells further comprise instructions that, when executed by the processor, cause the processor to: for a cell at an identified location predicted by the cell localization model: transform pixels of the intermediate mask representation at the identified location into binary values of a binary image; and determine a proportion of pixels at the identified location with a binary value that is indicative of the cell being pluripotent.

In various embodiments, the binary value indicative of the cell being pluripotent exceeds a threshold intensity value. In various embodiments, the instructions that cause the processor to generate pluripotency metrics for the plurality of cells further comprise instructions that, when executed by the processor, cause the processor to generate a pluripotency metric for each cell of the plurality of cells. In various embodiments, the non-transitory computer readable medium further comprises instructions that, when executed by the processor, cause the processor to identify one or more cells from the plurality of cells based on the generated pluripotency metrics, the identified one or more cells having pluripotency metrics indicating higher probability of pluripotency in comparison to non-identified cells.

In various embodiments, the predictive model is trained with paired contrast images and immunofluorescent images. In various embodiments, the predictive model is trained with paired contrast images and sequencing data. In various embodiments, the instructions that cause the processor to obtain the contrast image of the plurality of cells further comprises instructions that, when executed by the processor, cause the processor to capture the contrast image of the plurality of cells. In various embodiments, the instructions that cause the processor to obtain the contrast image of the plurality of cells further comprises instructions that, when executed by the processor, cause the processor to receive the contrast image of the plurality of cells. In various embodiments, the plurality of cells are cultured in vitro or ex vivo. In various embodiments, the plurality of cells are selected from any of induced pluripotent cells (iPSCs), embryonic stem cells, or cells derived from germ layers. In various embodiments, the plurality of cells are selected from any one of cells derived from an ectoderm layer, cells derived from a mesoderm layer, cells derived from an endoderm layer, embryonic stem cells, terminally differentiated cells, or pluripotent cells.

In various embodiments, the non-transitory computer readable medium further comprises instructions that, when executed by the processor, cause the processor to: generate a second set of pluripotency metrics for the plurality of cells; and determine changes in pluripotency in the plurality of cells using the generated pluripotency metrics and the second set of pluripotency metrics. In various embodiments, the non-transitory computer readable medium further comprises instructions that, when executed by the processor, cause the processor to: subsequent to the generation of pluripotency metrics for the plurality of cells and prior to the generation of the second set of pluripotency metrics for the plurality of cells, provide a treatment to the plurality of cells, wherein the determined changes in pluripotency is dependent at least in part on the provided treatment to the plurality of cells. In various embodiments, the contrast image is any of a brightfield image, phase-contrast image, dark-field image, Reinberg Illumination image, or polarization image. In various embodiments, the contrast image is captured using optical microscopy. In various embodiments, the predictive model achieves an accuracy of at least 0.90. In various embodiments, the predictive model achieves a precision of at least 0.90. In various embodiments, the predictive model achieves a recall of at least 0.75.

BRIEF DESCRIPTION OF THE DRAWINGS

These and other features, aspects, and advantages of the present invention will become better understood with regard to the following description and accompanying drawings. It is noted that wherever practicable similar or like reference numbers may be used in the figures and may indicate similar or like functionality. For example, a letter after a reference numeral, such as "third party entity 702A," indicates that the text refers specifically to the element having that particular reference numeral. A reference numeral in the text without a following letter, such as "third party entity 702," refers to any or all of the elements in the figures bearing that reference numeral (e.g. "third party entity 702" in the text refers to reference numerals "third party entity 702A" and/or "third party entity 702B" in the figures).

DETAILED DESCRIPTION OF THE INVENTION

Definitions

Terms used in the claims and specification are defined as set forth below unless otherwise specified.

The phrase "predictive model" refers to a pluripotency model and/or a cell localization model. In particular embodiments, "predictive model" used herein refers to both a pluripotency model and a cell localization model. In various embodiments, the pluripotency model and the cell localization model of the predictive are separate models and are separately implemented. In various embodiments, the pluripotency model and the cell localization model are structured together as a single predictive model. Thus, deployment of the predictive model can refer to joint deployment of the pluripotency model and the cell localization model. Additionally, training of the predictive model can refer to joint training of the pluripotency model and the cell localization model.

The phrase "pluripotency model" refers to a model that translates an image (e.g., image of cells) to an intermediate mask representation indicative of pluripotency of the plurality of cells in the image. In particular embodiments, the pluripotency model is a neural network model.

The phrase "cell localization model" refers to a model that determines spatial localization of one or more cells in the image. For example, the cell localization model can generate bounded structures that delineate locations of one or more cells in the image.

The term "antibody" is used in the broadest sense and specifically covers monoclonal antibodies (including full length monoclonal antibodies), polyclonal antibodies, multispecific antibodies (e.g., bispecific antibodies), and antibody fragments that are antigen-binding so long as they exhibit the desired biological activity, e.g., an antibody or an antigen-binding fragment thereof.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide").

It must be noted that, as used in the specification and the appended claims, the singular forms "a," "an" and "the" include plural referents unless the context clearly dictates otherwise.

Overview

Figure 1:
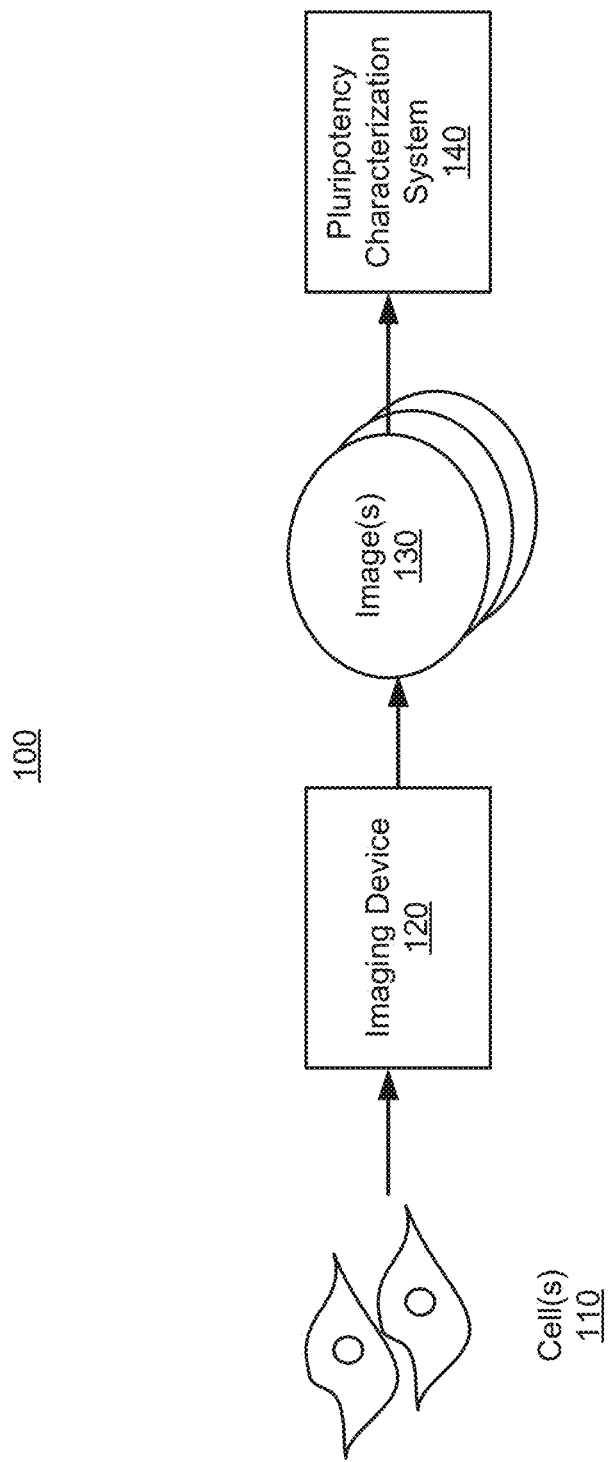
FIG. 1 depicts an overall system environment for predicting pluripotency of cells by analyzing images of the cells, in accordance with an embodiment.

FIG. 1 depicts an overall system environment for predicting pluripotency of one or more cells by analyzing images of the one or more cells, in accordance with an embodiment. Generally, an imaging device 120 is used to capture one or more images 130 of cells 110. The pluripotency characterization system 140 analyzes the images 130 to determine predicted pluripotency of the cells 110. In particular embodiments, the system environment 100 shown in FIG. 1 is useful for performing rapid, cheap, and non-destructive quality control checks to ensure that the cells 110 are exhibiting expected levels of pluripotency. For example, if the cells 110 have undergone a reprogramming protocol to generate induced pluripotent stem cells (iPSCs), the system environment 100 shown in FIG. 1 is useful for verifying whether the reprogramming protocol was successful in generating iPSCs that exhibit pluripotency. As another example, if the cells 110 are cells that have undergone a differentiation protocol, the overall process shown in FIG. 1 is useful for verifying whether the differentiation protocol was successful in propagating the cells 110 down a cellular lineage, as is evidenced by reduced levels of pluripotency. Thus, the cells 110 can be subsequently used based on the predicted pluripotency of the cells 110.

Cells

In various embodiments, the cells 110 shown in FIG. 1 refer to a population of cells. In various embodiments, the cells 110 shown in FIG. 1 refer to multiple populations of cells. In various embodiments, the cells 110 shown in FIG. 1 refer to a single cell. The cell(s) 110 can vary in regards to the type of cells (single cell type, mixture of cell types), cell lineage (e.g., cells in differing stages of maturation or differing stages of disease progression), or culture type (e.g., in vitro 2D culture, in vitro 3D culture, in vitro organoid or organ-on-chip systems, or ex vivo).

In various embodiments, the cells 110 are any one of cells derived from the ectoderm layer, cells derived from the mesoderm layer, cells derived from the endoderm layer, embryonic stem cells, mesodermal cells, terminally differentiated cells (e.g., A549 cells), or pluripotent cells. In various embodiments, mesodermal cells can be iStel cells.

In various embodiments, the cells 110 are an in vitro culture of cells that are cultured in a device that is conducive for imaging. For example, the cells 110 can be an in vitro culture of cells in a well plate (e.g., 6 well plate, 12 well plate, 24 well plate, 48 well plate, 96 well plate, 192 well plate, or 384 well plate). Such well plates or flasks can be clear bottom well plates for optical, fluorescence, or luminescence imaging.

In particular embodiments, the cells 110 are induced pluripotent stem cells (iPSCs) that have undergone a reprogramming protocol. For example, iPSCs can be generated through a variety of methods including reprogramming somatic cells using reprogramming factors Oct4, Sox2, Klf4, and Myc. Reprogramming of somatic cells can occur through viral or episomal reprogramming techniques. Examples methods for generating iPSCs are further described in PCT/US2018/067679, PCT/EP2009/003735, U.S. application Ser. No. 13/059,951, U.S. application Ser. No. 13/369,997, U.S. application Ser. No. 14/043,096, and U.S. application Ser. No. 13/441,328, each of which is hereby incorporated by reference in its entirety.

In particular embodiments, the cells 110 are differentiated cells (e.g., cells that have undergone a differentiation protocol). In various embodiments, the cells 110 are differentiated from cells that previously exhibited pluripotency, examples of which include stem cells (e.g., embryonic stem cells or iPSCs). In various embodiments, the cells 110 were differentiated from a primary cell (e.g., cells that underwent transdifferentiation).

In various embodiments, the cells 110 may have one or more engineered genetic changes. Thus, the system environment 100 shown in FIG. 1 can be implemented to determine or evaluate pluripotency of cells after the cells have undergone genetic changes. In various embodiments, the one or more genetic changes expressed by the cell are a result of overexpression of a particular cDNA. For example, a cDNA construct of a gene can be provided to the cell through a transfection method (e.g., lipofectamine) to introduce the one or more genetic changes. In various embodiments, the one or more genetic changes expressed by the cell are engineered using Clustered Regularly Interspaced Short Palindromic Repeats (CRISPR). For example, a CRISPR system for generating one or more genetic changes in a cell can include a CRISPR complex (with a CRISPR enzyme), one or more guide sequences for hybridizing with a target sequence to direct sequence-specific binding of the CRISPR complex to the target sequence. Gene editing using CRISPR systems is further described in U.S. Pat. Nos. 8,697,359, 8,697,359; 8,771,945; 8,795,965; 8,865,406; 8,871,445; 8,889,356; 8,895,308; 8,906,616; 8,932,814; 8,945,839; 8,993,233; 8,999,641, PCT/US2013/074611, and PCT/US2013/074819 each of which is hereby incorporated by reference in its entirety. In various embodiments, the one or more genetic changes expressed by the cell are engineered using Transcription Activator-like Effector Nuclease (TALENs). Gene editing using TALENs is further described in U.S. Pat. Nos. 9,353,378; 8,440,431; 8,440,432; 8,450,471; 8,586,363; 8,697,853; and 9,758,775, each of which is hereby incorporated by reference in its entirety. In various embodiments, one or more genetic changes expressed by the cell are engineered using Zinc finger nucleases. Gene editing using Zinc finger nucleases is further described in U.S. Pat. Nos. 7,888,121, 8,409,861, 7,951,925, 8,110,379, and 7,919,313, each of which is hereby incorporated by reference in its entirety.

In various embodiments, the cells 110 may have been exposed to a perturbation that promotes a cellular state in the cells 110. For example, the cellular state can be a diseased cellular state including a state where the cell exhibits differential gene expression, a state where the cell exhibits dysregulated behavior (e.g., abnormal cell cycle regulation, cell division, enzymatic function), a state where the cell expresses diseased proteins (e.g., proteopathies), and hypoxia, hyperoxia, hypocapnia, or hypercapnia induced states. Thus, the system environment 100 shown in FIG. 1 can be implemented to determine or evaluate pluripotency of cells after the cells have been exposed to the perturbation.

Examples of perturbations include a chemical agent, a molecular intervention, an environmental mimic or a gene editing agent. Examples of a gene editing agent include CRISPR nuclease system, such as CRISPR Cas9. Details regarding a CRISPR nuclease system, such as a CRISPR Cas9 system is described in WO2015/071474, which is incorporated by reference in its entirety. Additional examples of a gene editing agent include CRISPRi, and/or CRISPRa that serve to downregulate or overexpress certain genes, respectively. Further details regarding CRISPRi and CRISPRa and methods for transcriptional modulation using CRISPRi/a is described in U.S. application Ser. No. 15/326,428 and PCT/CN2018/117643, both which are hereby incorporated by reference in their entirety. Examples of chemical agent or a molecular intervention include genetic elements (e.g., RNA such as siRNA, shRNA, or mRNA, double or single stranded antisense oligonucleotides) as well as peptides, antibodies, cytokines, cholesterol crystals, free fatty acids, or A-beta aggregates. Examples of environmental mimics include $O_2$ tension, $CO_2$ tension, hydrostatic pressure, osmotic pressure, pH balance, ultraviolet exposure, temperature exposure or other physico-chemical manipulations.

Imaging Device and Images

The imaging device (e.g., imaging device 120 shown in FIG. 1) captures one or more images of the cells which can then be analyzed by the pluripotency characterization system 140. Generally, the imaging device is a device that can capture, through non-destructive means, images of live cells without impacting the viability of the cells. Therefore, the cells can be imaged using the imaging device, the images can be analyzed to determine the pluripotency of the cells, and the pluripotent cells can be selected and isolated for subsequent experimentation or use. In various embodiments, the imaging device 120 can be used to capture multiple images of a cell population over a time period. This enables the prediction and tracking of the pluripotency of cells in the cell population over the time period to understand how cellular pluripotency is changing within the cell population.

In various embodiments, the imaging device can capture an image of cells, wherein the cells are cultured in an in vitro 2D culture, in vitro 3D culture, in vitro organoid or organ-on-chip systems, or ex vivo. Thus, the imaging device may include a platform for housing the cells during imaging, such that the viability of the cultured cells are not impacted during imaging. In various embodiments, the imaging device may have a platform that enables control over the environment conditions that are exposed to the cells, thereby enabling live cell imaging. Environmental conditions can include gas content (e.g., $O_2$ or $CO_2$ content), humidity, temperature, cell culture media, and pH. Thus, by regulating environmental conditions over a time period, an imaging device can perform time-lapse imaging of the cells over the time period (e.g., over hours, days, or weeks).

In various embodiments, the imaging device 120 is capable of capturing a contrast image (e.g., an image based on differences in light intensity). Examples of a contrast image include any of a bright-field image, phase-contrast image, dark-field image, Reinberg Illumination image, or polarization image. In various embodiments, the imaging device captures an immunofluorescence image. In various embodiments, the imaging device captures an immunocytochemistry image. Example imaging devices capable of capturing a contrast image, immunofluorescence, or immunocytochemistry image include a light microscope, such as any of a brightfield microscope, darkfield microscope, phase-contrast microscope, differential interference contrast microscope, fluorescence microscope, confocal microscope, or two-photon microscope.

In particular embodiments, the imaging device captures an immunofluorescence image of cells that is informative for determining transcription profiles of the cells. In various embodiments, the imaging device captures an immunofluorescence image of cells that have undergone hybridization using one or more nucleic acid probes. Such methods are useful for performing spatial transcriptomics analysis, RNA fluorescent in situ hybridization, or sequential fluorescence in situ hybridization (SeqFISH+).

In various embodiments, the imaging device captures multiple images of the cells. In various embodiments, the imaging device captures multiple images of the cells simultaneously or substantially simultaneously (e.g., captured within 1 minute of each other, captured within 30 seconds of each other, captured within 10 seconds of each other, captured within 5 seconds of each other, captured within 1 second of each other). In various embodiments, the imaging device captures multiple images of the cells in succession so as to minimize spatial differences in the captured multiple images. In particular embodiments, the imaging device captures a contrast image and an immunofluorescent image. In particular embodiments, the imaging device captures a contrast image and an immunocytochemistry image. As described in further detail below, the multiple images captured of the cells can, in various embodiments, be included as a training example for use in training a pluripotency model.

Pluripotency Characterization System

The pluripotency characterization system 140 analyzes images captured of cells and predicts pluripotency metrics of the cells in the images. In various embodiments, the pluripotency characterization system 140 predicts pluripotency metrics for groups of cells. As an example, a group of cells can be a cell colony including cells that are in contact with one another. As another example, a group of cells can include cells within a particular location of the image (e.g., a quadrant in the image). In various embodiments, the pluripotency characterization system 140 predicts pluripotency metrics for individual cells in the image.

Figure 2:
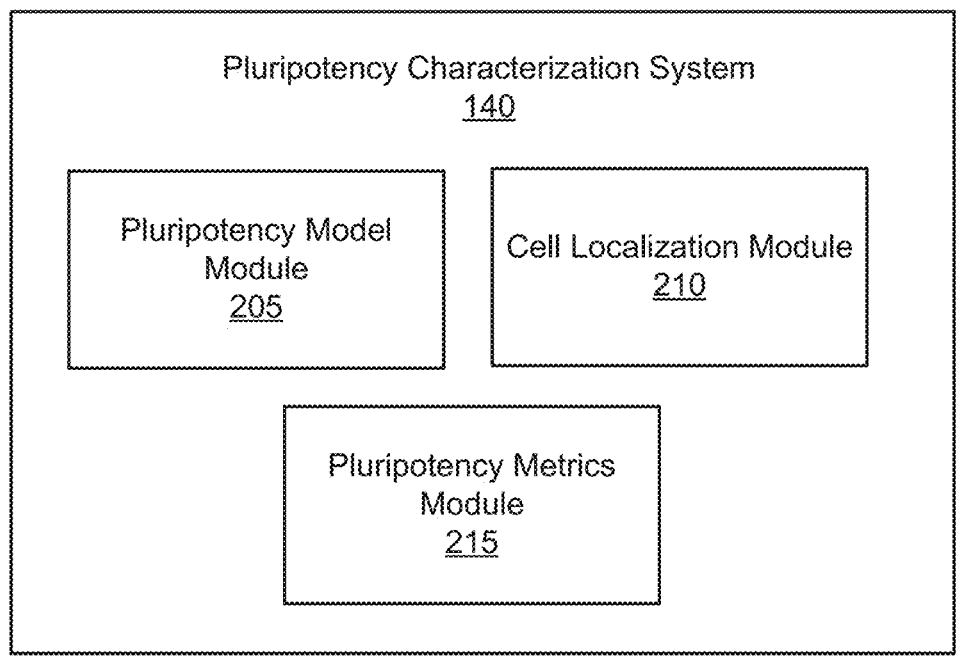
FIG. 2 depicts a block diagram of the pluripotency characterization system, in accordance with an embodiment.

FIG. 2 depicts a block diagram of the pluripotency characterization system 140, in accordance with an embodiment. As shown in FIG. 2, the pluripotency characterization system 140 includes a pluripotency model module 205, a cell localization module 210, and a pluripotency metrics module 215.

In various embodiments, the pluripotency model module 205 and the cell localization module 210 train and deploy a predictive model for predicting pluripotency metrics for cells. For example, the pluripotency model module 205 can train and deploy a first portion of the predictive model, hereafter referred to as a pluripotency model and the cell localization module 210 can train and deploy a second portion of the predictive model, hereafter referred to as a cell localization model. In such embodiments, the pluripotency model and the cell localization model together form the predictive model that enables prediction of pluripotency metrics for cells. Such a predictive model that includes both the pluripotency model and cell localization model is useful for predicting pluripotency metrics at the individual cell level. Although the description above refers to the pluripotency model and cell localization model as forming a first and second portion of a predictive model, respectively, in various embodiments, the pluripotency model and cell localization model can be two distinct models. Thus, references herein to a predictive model refer to either a single predictive model with two different portions (e.g., first portion made up of the pluripotency model and second portion made up of the cell localization model), or a predictive model with two distinct models (e.g., the pluripotency model is separate from the cell localization model).

Generally, the pluripotency model module 205 deploys a pluripotency model that translates an image (e.g., image of cells) to an intermediate mask representation indicative of pluripotency of the plurality of cells in the image. Generally, the intermediate mask representation is an approximation of known indicators of pluripotency. In various embodiments, the intermediate mask representation is an image with values that are indicative of pluripotency of the plurality of cells in the original image. In some embodiments, the intermediate mask representation may be an M×N image and each pixel of the M×N intermediate mask representation has a value that is informative as to whether the pixel is indicative of pluripotency. Such an intermediate mask representation is hereby referred to as an intensity mask. For example, each pixel may have an intensity value corresponding to intensity values of a known pluripotent biomarker. In various embodiments, the intermediate mask representation is a non-image based data structure with values that are indicative of pluripotency of the plurality of cells in the original image.

In various embodiments, the pluripotency model module 205 performs pre-processing tasks that enable the pluripotency model to analyze the image. In some embodiments, the pluripotency model module 205 can perform a feature extraction process that extracts features from the image and provides the extracted features as input to the pluripotency model. Thus, the pluripotency model analyzes the features of the image and predicts pluripotency of cells in the image based on the features. In some embodiments, the pluripotency model module 205 normalizes the image prior to deployment of the pluripotency model. For example, the pluripotency model module 205 may perform a z-score normalization on pixel values of the image. As another example, the pluripotency model module 205 may perform a normalization by dividing the pixel values by a constant value (such as a local or global max value). Generally, the normalization process preserves relative differences across different experimental conditions that were used to capture the images.

Referring to the cell localization module 210, it deploys a cell localization model that determines spatial localization of one or more cells in the image. For example, the cell localization model can generate bounded structures that delineate locations of one or more cells in the image. In various embodiments, the cell localization model generates bounding structures around groups of cells e.g., a colony of cells. For example, the cell localization model can generate bounding structures around groups of cells based on the proximity of cells to one another in the group. Cells that are close in proximity to one another are grouped together in a colony and can have a bounding structure around them, whereas cells far in proximity are grouped in separate colonies and therefore, have separate bounding structures around them. In particular embodiments, the cell localization model generates bounding structures around individual cells in the image. In various embodiments, the output of the cell localization model is an image including the cells overlaid with bounding structures that spatially delineate one or more cells in the image.

Referring to the pluripotency metrics module 215, it determines pluripotency metrics for one or more cells in an image. In various embodiments, the pluripotency metrics module 215 determines one pluripotency metric for the population of cells in the image. For example, the pluripotency metrics module 215 determines a percentage of pluripotent cells in the image. In various embodiments, the pluripotency metrics module 215 determines more than one pluripotency metric for the cells in the image. In some embodiments, the pluripotency metrics module 215 partitions the image into regions and determines a pluripotency metric for one or more of the regions that reflects the pluripotency of cells in the one or more of the regions. For example, the pluripotency metrics module 215 can partition the image into X number of regions and determine a pluripotency metric for each region that reflects the pluripotency of cells in the region. In various embodiments, the pluripotency metrics module 215 determines pluripotency metrics at the cellular level. Therefore, the pluripotency metrics module 215 assigns a first pluripotency metric to a first cell, a second pluripotency metric to a second cell, and so on. This enables an understanding of the pluripotency of each individual cell, which can facilitate the selection and isolation of individual cells (e.g., cells identified as pluripotent and non-pluripotent), as is described in further detail herein.

In various embodiments, the pluripotency metrics module 215 determines pluripotency metrics for one or more cells by determining a proportion of values in the intermediate mask representation that are indicative of pluripotent cells. For example, in scenarios in which the intermediate mask representation is an image, the pluripotency metrics module 215 categorizes pixels in the intermediate mask representation as either pluripotent pixels or non-pluripotent pixels. Thus, the pluripotency metrics module 215 determines pluripotency metrics, such as a percentage of cells in the image that are pluripotent. In various embodiments, the pluripotency metrics module 215 determines a percentage of total cells in the image that are pluripotent. In various embodiments, the pluripotency metrics module 215 determines a percentage of cells in a colony in the image that are pluripotent. In various embodiments, the pluripotency metrics module 215 determines a percentage of cells in multiple colonies that are pluripotent. In various embodiments, the pluripotency metrics module 215 determines pluripotency of individual cells.

In various embodiments, the pluripotency metrics module 215 uses both the intermediate mask representation (generated by the pluripotency model) and cell localizations (generated by the cell localization model) to generate pluripotency metrics for cells. For example the pluripotency metrics module 215 can categorize pixels (e.g., pixels from the intermediate mask representation) located within a bounding structure (e.g., bounding structure of the cell localizations) as either pluripotent pixels or non-pluripotent pixels. Thus, for a cell delineated by the bounding structure, the pluripotency metrics module 215 determines a number or percentage of pluripotent pixels corresponding to the cell. As such, the pluripotency metrics module 215 makes a call as to whether the cell is pluripotent or non-pluripotent based on the number or percentage of pluripotent pixels corresponding to the cell.

In various embodiments, the pluripotency metrics module 215 performs a thresholding of pixels of the intermediate mask representation or pixels within a bounding structure. Pixels with a value above a threshold value are categorized in one class (e.g., pluripotent pixel) and pixels of the intermediate mask representation with a value below the threshold value are categorized in a second class (e.g., non-pluripotent pixel). In various embodiments, the threshold value is a normalized value between 0 and 1, such as 0.1, 0.2, 0.4, 0.5, 0.6, 0.7, 0.8, or 0.9. In particular embodiments, the threshold value is 0.5.

In various embodiments, the pluripotency metrics module 215 directly categorizes pixels of the intermediate mask representation or pixels within a bounding structure into separate classes (e.g., pluripotent pixels or non-pluripotent pixels) based on the raw intensity values of the pixels. Thus, pixels of the intermediate mask representation or pixels within a bounding structure with a raw intensity value above a threshold are categorized in one class (e.g., pluripotent pixel) and pixels of the intermediate mask representation with a raw intensity value below the threshold value are categorized in a second class (e.g., non-pluripotent pixel). In various embodiments, the threshold value is a percentage of a maximum raw intensity value. For example, the threshold value can be 50% of a maximum raw intensity value. In various embodiments, the threshold value is 10%, 20%, 30%, 40%, 50%, 60%, 70%, 80%, or 90% of a maximum raw intensity value.

The pluripotency metrics module 215 can determine the total number of pixels of the intermediate mask representation or pixels within a bounding structure that are categorized in a class including pluripotent pixels. As one example, by determining the total number of pixels of the intermediate mask representation that are categorized in a class including pluripotent pixels, the pluripotency metrics module 215 can generate pluripotency metrics reflecting the total percentage of pixels in the intermediate mask representation that are indicative of pluripotent cells. As another example, the pluripotency metrics module 215 generates pluripotency metrics reflecting the total percentage of pluripotent cells or total percentage of non-pluripotent cells out of all possible cells in the image.

As yet another example, by determining the total number of pixels within a bounding structure that are categorized in a class including pluripotent pixels, the pluripotency metrics module 215 can generate a pluripotency metric reflecting the total percentage of pixels in a bounding structure that are indicative of the cell being pluripotent. If over a threshold percentage of pixels in the bounding structure indicate that the cell is pluripotent, then the pluripotency metrics module 215 can label the cell as a pluripotent cell. Conversely, if under a threshold percentage of pixels in the bounding structure indicate that the cell is pluripotent, then the pluripotency metrics module 215 can label the cell as a non-pluripotent cell. In various embodiments, the threshold percentage of pixels can be any one of 10%, 15%, 20%, 25%, 30%, 35%, 40%, 45%, 50%, 55%, 60%, 65%, 70%, 75%, 80%, 85%, 90%, or 95%. In particular embodiments, the threshold percentage of pixels is 10%. In particular embodiments, the threshold percentage of pixels is 25%. In particular embodiments, the threshold percentage of pixels is 50%. The pluripotency metrics module 215 can repeat the process above to further determine pluripotency metrics for additional cells in the image that are delineated by bounding structures.

Flow Diagram of Deploying Predictive Model

Figure 3:
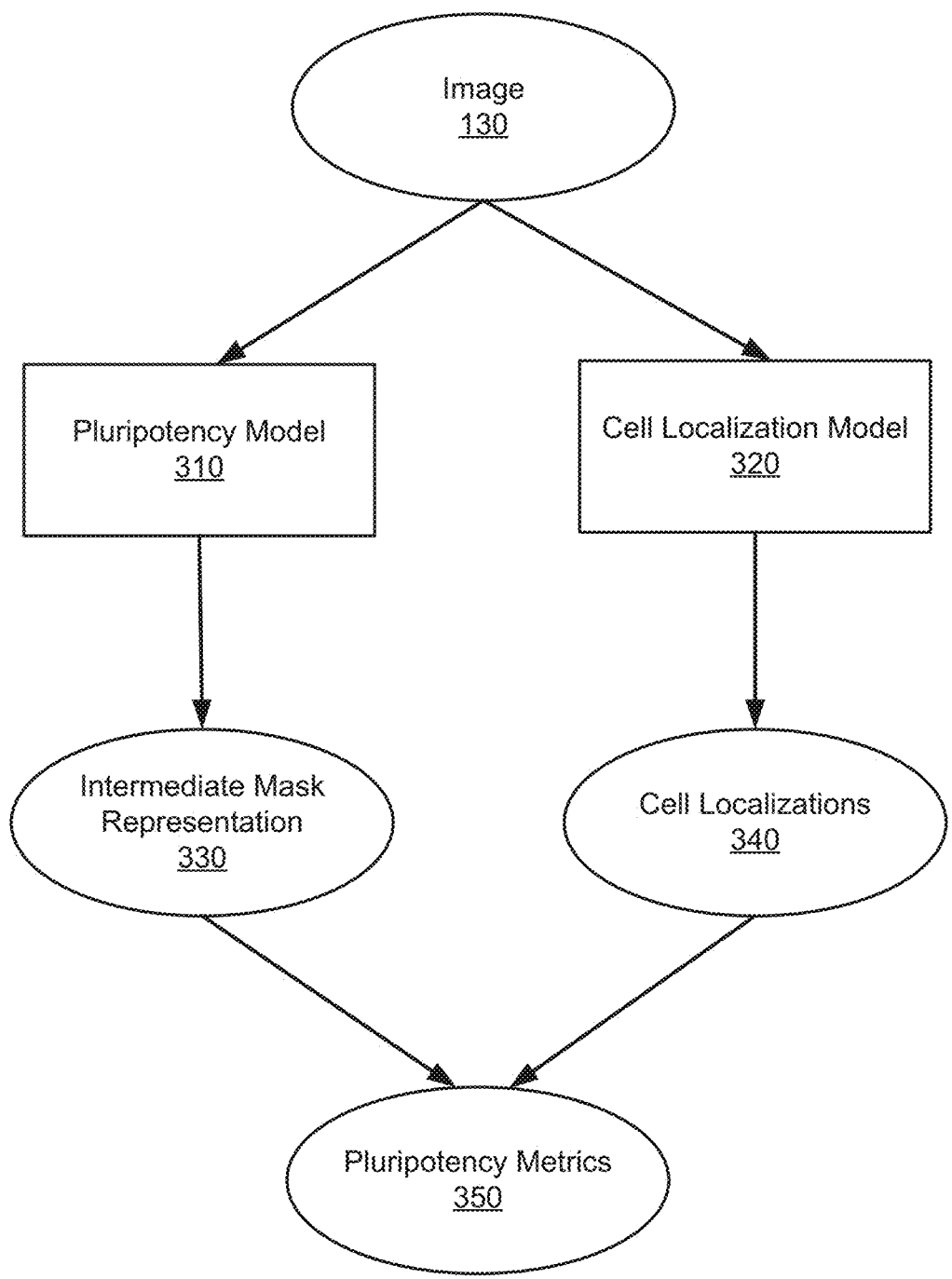
FIG. 3 depicts a flow diagram for predicting pluripotency metrics of cells in an image, in accordance with an embodiment.

Reference is now made to FIG. 3, which depicts a flow diagram for predicting pluripotency metrics of cells in an image, in accordance with an embodiment. As shown in FIG. 3, an image 130 is analyzed by the pluripotency model 310 and the cell localization model 320. In various embodiments, the pluripotency model 310 and the cell localization model 320 independently analyze the image 130. In various embodiments, the pluripotency model 310 and the cell localization model 320 analyze the image 130 simultaneously. In various embodiments, the pluripotency model 310 and the cell localization model 320 analyze the image 130 sequentially. For example, the pluripotency model 310 analyzes the image 130 first, and then the cell localization model 320 analyzes the image 130. As another example, the cell localization model 320 analyzes the image 130 first, and then the pluripotency model 310 analyzes the image 130.

Specifically, the pluripotency model 310 translates an image 130 to an intermediate mask representation 330 and the cell localization model 320 generates cell localizations 340 for one or more cells in the image 130. The intermediate mask representation 330 and the cell localizations 340 are combined to generate pluripotency metrics 350 for one or more cells in the image 130. In various embodiments, pluripotency metrics 350 are generated for a population of cells. An example of such pluripotency metrics 350 include the percentage of pluripotent cells in the population of cells. In various embodiments, pluripotency metrics 350 are generated for individual cells. An example of such pluripotency metrics 350 include indications identifying whether individual cells in the image are pluripotent or not pluripotent.

Structure and Training of Pluripotency Model and Cell Localization Model

Generally, the pluripotency model 310 is trained to translate an image including one or more cells to an intermediate mask representation 330 with values that are indicative of pluripotency of the one or more cells in the image. The cell localization model 320 is trained to analyze the image including one or more cells and to generate bounding structures around individual cells in the image. In various embodiments, the pluripotency model 310 and the cell localization model 320 can individually be any one of a regression model (e.g., linear regression, logistic regression, or polynomial regression), decision tree, random forest, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks).

In particular embodiments, the pluripotency model 310 is a neural network. In particular embodiments, the pluripotency model 310 is a neural network with at least one downsampling layer and at least one upsampling layer. In particular embodiments, the pluripotency model 310 is a neural network with one or more skip connections such that the output of one layer serves as input to multiple subsequent layers (instead of only the next layer).

In particular embodiments, the cell localization model 320 is a neural network. The cell localization model 320 can analyze an image including cells and determines spatial locations of the cells. In various embodiments, the cell localization model 320 is trained to predict spatial locations of cells using ground truth images in which spatial locations of cells were previously determined. For example, spatial locations of cells in ground truth images can be determined by employing a nuclei segmentation algorithm that determines the locations of cell nuclei, which serve as a proxy for locations of corresponding cells. Further examples of nuclei segmentation processes are described in Hernandez, C. et al. Using Deep Learning for Segmentation and Counting within Microscopy Data, 2018, arXiv:1802.10548, Araujo, F., et al, Deep learning for cell image segmentation and ranking, Comput Med Imaging Graph. 2019; 72: 13-21, and Stringer. C., Wang, T., Michaelos. M. et al. Cellpose: a generalist algorithm for cellular segmentation. *Nat Methods* 18, 100-106 (2021), each of which is hereby incorporated by reference in its entirety.

The pluripotency model 310 and/or the cell localization model 320 can each be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, gradient descent, and dimensionality reduction techniques such as manifold learning, principal component analysis, factor analysis, autoencoder regularization, and independent component analysis, or combinations thereof. In various embodiments, the pluripotency model and/or the cell localization model is trained using supervised learning algorithms, unsupervised learning algorithms, semi-supervised learning algorithms (e.g., partial supervision), weak supervision, transfer, multi-task learning, or any combination thereof. In particular embodiments, the pluripotency model 310 and/or the cell localization model 320 is trained through iterations of stochastic gradient descent to minimize a loss function.

In various embodiments, the pluripotency model 310 and/or the cell localization model 320 have one or more parameters, such as hyperparameters or model parameters. Hyperparameters are generally established prior to training Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, and coefficients in a regression model. The model parameters of the pluripotency model 310 and/or the cell localization model 320 are trained (e.g., adjusted) using the training data to improve the predictive power of the pluripotency model and/or the cell localization model.

Figure 4:
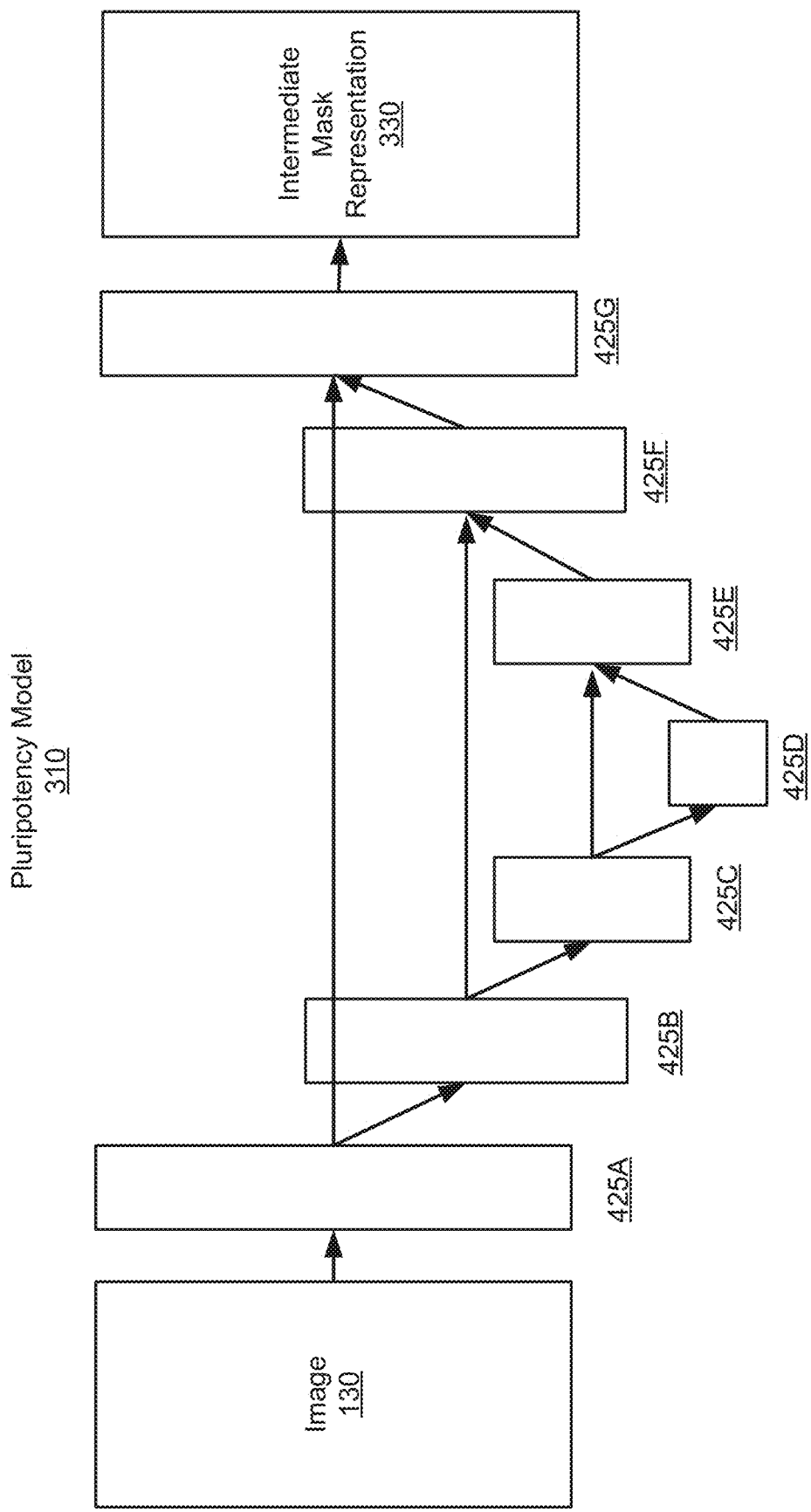
FIG. 4 depicts an example structure of a pluripotency model, in accordance with an embodiment.

FIG. 4 depicts an example structure of a pluripotency model 310, in accordance with an embodiment. Specifically, FIG. 4 depicts a pluripotency model 310 that translates an image 130 including one or more cells to an intermediate mask representation 330 with values that are indicative of a pluripotency of the one or more cells in the image 130. In various embodiments, the output of the pluripotency model is an intermediate mask representation 330 with the same spatial resolution as the input image 130 where each pixel of the intermediate mask representation 330 is a prediction of a pluripotent biomarker expression at the corresponding pixel in the input image 130.

In various embodiments, the image 130 may be an original image captured by an imaging device. In various embodiments, the image 130 is a pre-processed image. In various embodiments, the image 130 may be a randomly sampled image derived from the original image captured by an imaging device. As a specific example, the image 130 may be an image with a resolution of 256×256 that is randomly sampled from an original image acquired at a field of view level of 1992×1992 resolution.

The pluripotency model 310 includes one or more layers (e.g., layer 425A, 425B, 425C, 425D, 425E, 425F, and 425G) that translates the image 130 to the intermediate mask representation 330. In various embodiments, each of one or more of the layers 425 involve nonlinear transforms. In various embodiments, each of one or more of the layers 425 involve nonlinear transforms that modify the spatial resolution of the input to the layer. For example, as shown in FIG. 4, the pluripotency model 310 may include a layer 425A that reduces the spatial resolution of the image 130 and feeds a representation with reduced spatial resolution to at least the next layer (e.g., layer 425B).

In various embodiments, the pluripotency model 310 includes downsampling operators. In various embodiments, the pluripotency model 310 includes upsampling operators. In various embodiments, the pluripotency model 310 includes downsampling and upsampling operators. For example, as shown in FIG. 4, the pluripotency model 310 can include downsampling operators that downsample the image 130 through downsampling layers 425A, 425B, and 425C to a representation at layer 425D. To provide an example, the original image 130 may have a spatial resolution of M×N where M and N represent the number of pixels in each dimension. In various embodiments, M=1992 and N=1992. Here, layer 425A may intake the image 130 at the spatial resolution of M×N and output a representation at a lower spatial resolution. Through subsequent downsampling layers 425B, 425C, the representation at layer 425D is at a further lower spatial resolution. For example, the representation at layer 425D may have a spatial resolution of M/P×N/Q where P and Q are constant values.

The pluripotency model 310 can further include upsampling operators that upsample the representation at layer 425D through upsampling layers 425E, 425F, and 425G to generate the intermediate mask representation 330. In various embodiments, the representation at layer 425D has a spatial resolution of M/P×M/Q where P and Q are constant values. Through subsequent upsampling layers 425E, 425F, and 425G, the output intermediate mask representation 330 has a spatial resolution of M×N.

In various embodiments, the representation at one layer of the pluripotency model 310 has the same spatial resolution at another layer of the pluripotency model 310. For example, a representation at a downsampling layer of the pluripotency model 310 can have the same spatial resolution as a representation at an upsampling layer of the pluripotency model 310. As a specific example, a representation at downsampling layer 425A can have the same spatial resolution as a representation at upsampling layer 425G. A representation at downsampling layer 425B can have the same spatial resolution as a representation at upsampling layer 425F. A representation at downsampling layer 425C can have the same spatial resolution as a representation at upsampling layer 425E.

In various embodiments, the pluripotency model 310 includes one or more skip connections such that the output of a first layer serves as the input to a subsequent layer that is not immediately after the first layer. For example, as shown in FIG. 4, the output of layer 425A can serve as input to layer 425G. As shown in FIG. 4, the output of layer 425B can serve as input to layer 425F. As shown in FIG. 4, the output of layer 425C can serve as input to layer 425E. The implementation of skip connections enables the pluripotency model 310 to learn local features within the image 130.

Although FIG. 4 depicts a pluripotency model 310 that includes three downsampling layers (e.g., layers 425A, 425B, and 425C) and three upsampling layers (e.g., layers 425E, 425F, and 425G), in various embodiments, the pluripotency model 310 can include additional or fewer upsampling and/or downsampling layers.

Figure 5A:
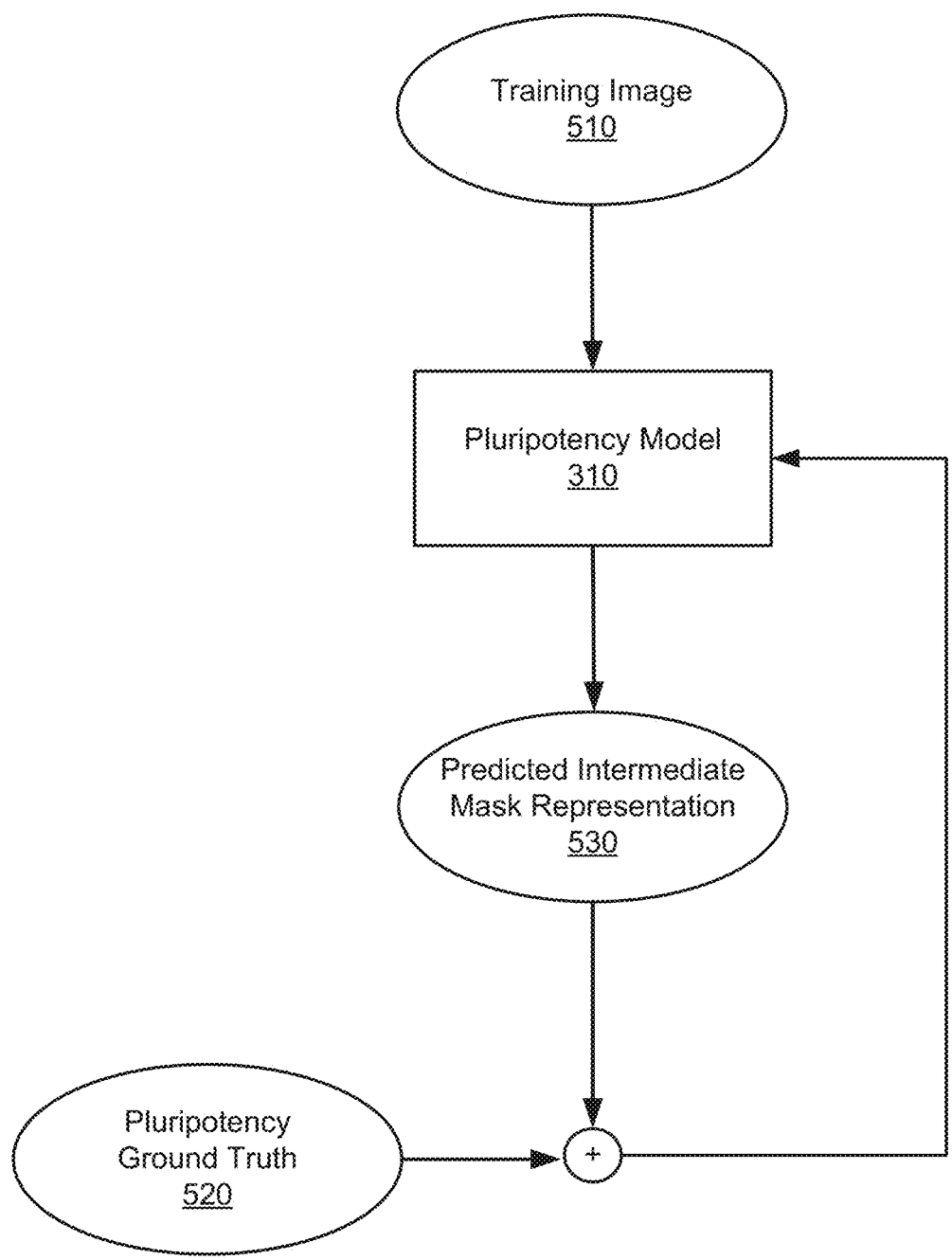
FIG. 5A depicts a flow diagram for training a pluripotency model, in accordance with an embodiment.

FIG. 5A depicts a flow diagram for training a pluripotency model, in accordance with an embodiment. In various embodiments, the pluripotency model 310 can be iteratively trained using multiple training examples, such that the pluripotency model 310 is trained to improve its prediction (e.g., predicted intermediate mask representation 530) over successive training iterations. For example, over successive training iterations, the parameters of the pluripotency model 310 are adjusted such that the pluripotency model 310 improves its prediction (e.g., predicted intermediate mask representation 530) over subsequent training examples.

FIG. 5A shows a training iteration for training the pluripotency model 310. Here, a training example used for training the pluripotency model 310 includes a training image 510 that is paired with a ground truth (e.g., pluripotency ground truth 520). In particular embodiments, the training image 510 includes a contrast image.

The pluripotency model 310 analyzes the training image 510 of a training example and generates a predicted intermediate mask representation 530. The predicted intermediate mask representation 530 is compared to the pluripotency ground truth 520 and the pluripotency model 310 is trained based on the comparison. For example, the pluripotency model 310 is trained based on the difference between the predicted intermediate mask representation 530 and the pluripotency ground truth 520. In various embodiments, the difference between the predicted intermediate mask representation 530 and the pluripotency ground truth 520 is back-propagated to adjust the parameters of the pluripotency model 310. In particular embodiments, a loss function is used for training the pluripotency model 310. In particular embodiments, cross entropy is employed as the loss function.

Generally, the pluripotency ground truth 520 is ground truth data that provides a known measure of the pluripotency of one or more cells in a sample. For example, the pluripotency ground truth 520 is paired to the training image 510 and therefore, the pluripotency ground truth 520 provides a known measure of the pluripotency of cells captured in the training image 510.

In various embodiments, the pluripotency ground truth 520 is an image of one or more cells. In such embodiments, a training example includes paired images captured from a single sample. For example, the training image 510 is a first image of the training example, and the pluripotency ground truth 520 is a second image of the training example. In various embodiments, a training example can include a pair of images of a single sample including one or more cells that were captured using a single imaging device. In various embodiments, the pair of images can be captured simultaneously or substantially simultaneously (e.g., captured within 1 minute of each other, captured within 30 seconds of each other, captured within 10 seconds of each other, captured within 5 seconds of each other, captured within 1 second of each other).

In various embodiments, the pluripotency ground truth 520 is an immunocytochemistry image. In various embodiments, the pluripotency ground truth 520 is an immunofluorescent image. Here, one or more sample preparation protocols can be performed to stain for one or more pluripotency markers (e.g., using fluorescently labeled antibodies) such that the pluripotency ground truth 520 includes measurable pluripotency markers. Example pluripotency markers can be biomarkers such as any one of Octamer-binding protein 4 (Oct4, UniProt: Q01860), SRY-Box Transcription Factor 2 (Sox2, UniProt: P48431), Kruppel Like Factor 4 (Klf4, UniProt: O43474), c-Myc (UniProt: P01106), Nanog (Uniprot: Q959S0), Lin28 (Uniprot: Q9H9Z2), SSEA-4, Tra-1-60, Tra-1-81, Alkaline Phosphatase, CD9 (UniProt: P21926), E-cadherin (UniProt: P12830), and Podocalyxin Like (PODXL, UniProt: O00592). Thus, returning to FIG. 5A, the pluripotency model 310 is trained to predict a predicted intermediate mask representation 530 including predicted values of one or more pluripotency markers. Thus, the predicted values of the one or more pluripotency markers of the predicted intermediate mask representation 530 are compared to the true values of the one or more pluripotency markers of the pluripotency ground truth 520 for purposes of training the pluripotency model 310.

In various embodiments, the pluripotency ground truth 520 includes sequencing profiles that are indicative of the pluripotency of the one or more cells. For example, the pluripotency ground truth 520 can include transcriptional sequencing profiles and/or epigenetic profiles of one or more cells in a sample, where the transcriptional sequencing profiles are indicative of the pluripotency of the one or more cells. The transcriptional sequencing profile can be generated for the one or more cells in the sample using any of bulk RNA sequencing, single cell RNA sequencing, or Assay for Transposase Accessible Chromatin (ATAC-seq). Specific transcriptional sequencing profiles (e.g., expression of a gene or combinations of genes) or epigenetic profiles (e.g., modifications to expression of a gene or combinations of genes) can be indicative of cellular pluripotency. For example, transcriptional sequencing profiles indicative of cellular pluripotency can include expression of specific genes that are known to be correlated to cellular pluripotency. Transcriptional sequencing profiles indicative of cellular pluripotency can include gene expression of Oct4, Sox2, Klf4, c-Myc, Nanog, Lin28, SSEA-4, Tra-1-60, Tra-1-81, Alkaline Phosphatase, CD9, E-cadherin, and PODXL. Epigenetic profiles indicative of cellular pluripotency can include histone or DNA methylation statuses, presence of bivalent chromatin (e.g., any of acetylation at lysine 9, trimethylation at lysine 4 of histone H3, trimethylation at lysine 27 of histone H3), X-inactivation status, and/or presence of polycomb complexes that are known to be correlated to cellular pluripotency. Thus, returning to FIG. 5A, the pluripotency model 310 is trained to predict a predicted intermediate mask representation 530 including predicted values of a sequencing profile (e.g., transcriptional sequencing profile and/or epigenetic profile) or cells in a sample. Thus, the predicted values of the sequencing profile of the predicted intermediate mask representation 530 are compared to the true values of the sequencing profile of the pluripotency ground truth 520 for purposes of training the pluripotency model 310.

In various embodiments, the pluripotency ground truth 520 includes one or more images indicative of transcriptional profiles of one or more genes known to be correlated to cellular pluripotency. Example genes known to be correlated to cellular pluripotency include any of Oct4, Sox2, Klf4, c-Myc, Nanog, Lin28, SSEA-4, Tra-1-60, Tra-1-81, Alkaline Phosphatase, CD9, E-cadherin, and PODXL In various embodiments, the transcriptional profiles represent mRNA expression of the one or more genes known to be correlated to cellular pluripotency. In various embodiments, a transcriptional profile refers to mRNA expression of a single gene known to be correlated to cellular pluripotency. In various embodiments, a transcriptional profile refers to mRNA expression of 2 or more genes known to be correlated to cellular pluripotency. In various embodiments, a transcriptional profile refers to mRNA expression of 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 25 or more, 30 or more, 35 or more, or more, 45 or more, 50 or more, 60 or more, 70 or more, 80 or more, 90 or more, or 100 or more genes.

In some embodiments, the pluripotency ground truth 520 includes one or more images indicative of transcriptional profiles of one or more genes that are determined via RNA fluorescent in situ hybridization (RNA-FISH). RNA-FISH is a method to detect and localize messenger ribonucleic acid (mRNA) within the cellular context without the need to remove the cell from the surface it is growing to isolate the mRNA. Generally, RNA-FISH involves the development and use of nucleic acid probes, such as fluorescently labeled nucleic acid probes, which hybridize with target nucleic acid sequences. For example, a nucleic acid probe can be designed to hybridize with a mRNA transcript from a gene known to be correlated to cellular pluripotency. Nucleic acid probes can be DNA, cDNA, or RNA, can be single or double-stranded, and/or can range in length (e.g., from 20 bases to over 1000 bases). RNA-FISH can involve a set of processing steps including 1) tissue/cell preparation, 2) nucleic acid probe hybridization, 3) washing to remove unbound probes, and 4) fluorescent imaging to capture fluorescent signal of the hybridized probe.

Tissue and/or cell preparation can involve fixing the cell or tissue. For example, fixatives such as formalin, formaldehyde, paraformaldehyde, glutaraldehyde, or alcohol-based fixatives (e.g., ethanol or methanol) can be implemented to fix cells or tissues in place for in situ hybridization. Tissues or cells can be permeabilized to improve permeability (e.g., for improved access of nucleic acid probes). Permeabilization agents include detergents and proteases (e.g., proteinase K). Once cells or tissues are fixed and permeabilized, the nucleic acid probes (e.g., fluorescently tagged nucleic acid probes) are provided to hybridize with target nucleic acids. In various embodiments, different nucleic acid probes with different fluorophores can be provided to hybridize with different target nucleic acids. For example, a first nucleic acid probe with a first fluorophore can hybridize with a Nanog mRNA transcript whereas a second nucleic acid probe with a second fluorophore can hybridize with a Oct4 mRNA transcript. Thus, mRNA expression for multiple genes can be determined as long as the different fluorophores can be effectively distinguished (e.g., via different fluorescent channels of a fluorescent microscope). Following hybridization, unbound nucleic acid probe molecules are washed out to eliminate background signal. Thus, the remaining hybridized nucleic acid probes can be imaged and their corresponding fluorescent signals are captured (e.g., via fluorescent microscopy) to determine mRNA expression levels of one or more genes. These captured fluorescent images can serve as the pluripotency ground truth 520 for training the pluripotency model 310, as shown in FIG. 5A. Further details of RNA-FISH are described in Buxbaum, A. et al., Single β-Actin mRNA Detection in Neurons Reveals a Mechanism for Regulating Its Translatability, Science 343, 419-422 (2014) and Young, A. P., et al., (2020). A technical review and guide to RNA fluorescence in situ hybridization. PeerJ, 8, e8806, each of which is hereby incorporated by reference in its entirety.

In some embodiments, the pluripotency ground truth 520 includes one or more images indicative of transcriptional profiles of one or more genes that are determined via sequential fluorescence in situ hybridization (SeqFISH+). SeqFISH+ represents a version of spatial transcriptomics which allows visualization and quantitative analysis of the transcriptome with spatial resolution of an individual cell. For example, SeqFISH+ can be implemented to detect mRNA transcripts for 10,000 genes in single cells with high accuracy. Generally, SeqFISH+ involves repeatedly performing the RNA-FISH process, as described above, through a sequential stripping and hybridization process. For example, during a first iteration, a nucleic acid probe can be provided to hybridize with a first mRNA transcript from a first gene known to be correlated to cellular pluripotency. Thus, the fluorescent signal of the nucleic acid probe is captured (e.g., via fluorescent microscopy) to determine the expression of the first gene. Next, a strip-wash step can be implemented to remove the fluorescence of the nucleic acid probe that is hybridized with the first mRNA transcript. In various embodiments, probe stripping can involve washing using a wash buffer (e.g., saline sodium citrate (SSC) buffer), formamide, and/or ethanol. Following the strip wash, a second iteration can be performed. Here, the second iteration can involve a rehybridization step using a new nucleic acid probe that is designed to hybridize with a second mRNA transcript from a second gene known to be correlated to cellular pluripotency. Thus, the fluorescent signal of the new nucleic acid probe can be captured (e.g., via fluorescent microscopy) to determine the expression of the second gene. The strip wash and rehybridization process can be further repeated for additional nucleic acid probes.

In various embodiments, at each iteration, more than one nucleic acid probe can be used for hybridizing with mRNA transcripts from multiple genes. For example, at each iteration, two, three, four, or five different nucleic acid probes can be used, where each of the different nucleic acid probes has a different fluorophore. Thus, the fluorescent signals of the different nucleic acid probes can be captured at each iteration to determine mRNA transcript expression of two, three, four, or five different genes. Therefore, at a subsequent iteration, the expression of an additional two, three, four, or five genes can be investigated by designing corresponding nucleic acid probes with different fluorophores. The iterations can be sequentially performed (e.g., via sequential strip wash and rehybridization steps) to determine gene expression of larger numbers of genes (e.g., genes correlated with pluripotency). Further details of SeqFISH+ are described in Eng, CH. L., Lawson, M., Zhu, Q. et al. Transcriptome-scale super-resolved imaging in tissues by RNA seqFISH+. Nature 568, 235-239 (2019) and Hu, L. et al, A molecular pathology method for sequential fluorescence in situ hybridization for multi-gene analysis at the single-cell level. Oncotarget 8(31): 50534-50541 (2017), each of which is hereby incorporated by reference in its entirety.

Returning to FIG. 5A, in various embodiments, the pluripotency ground truth 520 may be an image representing a combination of a plurality of images. By combining a plurality of images to generate the pluripotency ground truth 520, the resulting pluripotency ground truth 520 may represent a more robust pluripotency signal across one or more genes. For example, as described above, by performing RNA-FISH or SeqFISH+, different fluorescent images corresponding to different genes can be captured. A first fluorescent image can include fluorescent signals indicative of expression of a first gene (e.g., a first gene correlated with pluripotency), and a second fluorescent image can include fluorescent signals indicative of expression of a second gene (e.g., a second gene correlated with pluripotency). In such embodiments, the first fluorescent image and the second fluorescent image may be combined to generate the pluripotency ground truth 520 that is used to train the pluripotency model 310.

In various embodiments, the pluripotency ground truth 520 may be an image that represents a combination of a plurality of images of different cellular analytes (e.g., DNA, RNA, or protein expression) that are indicative of pluripotency of cells. For example, as described above, a first fluorescent image can be captured via SeqFISH+ which indicates presence or absence of RNA transcripts corresponding to a particular pluripotent gene. A second fluorescent image may be captured of fluorescently stained proteins (e.g., stained via fluorescently labeled antibodies) for the same gene or of a different gene. Thus, the first fluorescent image and the second fluorescent image may be combined to generate the pluripotency ground truth 520.

In various embodiments, combining the first fluorescent image and the second fluorescent image involves averaging e.g., on a per-pixel basis, fluorescent intensities of the first fluorescent image and the second fluorescent image. In various embodiments, more than two fluorescent images can be combined to generate the pluripotency ground truth 520. For example, three or more, four or more, five or more, six or more, seven or more, eight or more, nine or more, or ten or more different fluorescent images can be combined to generate the pluripotency ground truth 520. Here, each of the different fluorescent images may include fluorescent signals indicative of expression of a different gene.

Figure 5B:
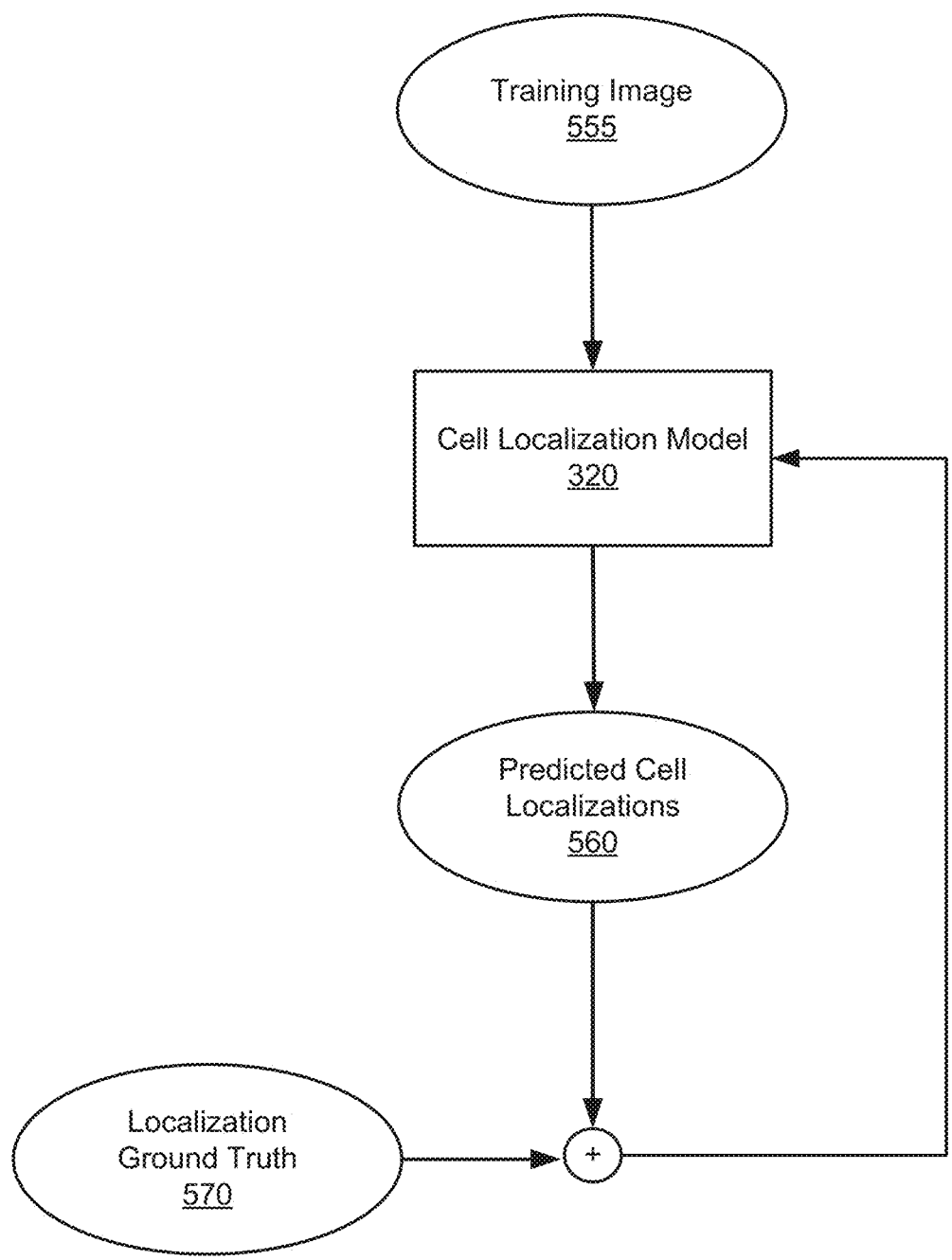
FIG. 5B depicts a flow diagram for training a cell localization model, in accordance with an embodiment.

FIG. 5B depicts a flow diagram for training a cell localization model 320, in accordance with an embodiment. In various embodiments, the cell localization model 320 can be iteratively trained using multiple training examples, such that the cell localization model 320 is trained to improve its prediction (e.g., predicted cell localizations 560) over successive training iterations. For example, over successive training iterations, the parameters of the cell localization model 320 are adjusted such that the cell localization model 320 improves its prediction (e.g., predicted cell localizations 560) over subsequent training examples.

FIG. 5B shows a training iteration for training the cell localization model 320. Here, a training example used for training the cell localization model 320 includes a training image 555 that is paired with a ground truth (e.g., localization ground truth 570). In particular embodiments, the training image 555 includes a contrast image. In various embodiments, the training image 555 may be the same image as training image 510 shown in FIG. 5A and used to train the pluripotency model 310.

The cell localization model 320 analyzes the training image 555 of a training example and generates predicted cell localizations 560. In various embodiments, the predicted cell localizations 560 includes predicted bounding structures around one or more cells that identify the spatial localization of the one or more cells in the training image 555. The predicted cell localizations 560 is compared to the localization ground truth 570, and the cell localization model 320 is trained based on the comparison. Here, the localization ground truth 570 may represent a ground truth image with identified spatial locations of cells in the ground truth image. In various embodiments, the difference between the predicted cell localizations 560 and the localization ground truth 570 is used to train the cell localization model 320. In various embodiments, the difference between the predicted cell localizations 560 and the localization ground truth 570 is backpropagated to adjust the parameters of the cell localization model 320. In particular embodiments, a loss function is used for training the cell localization model 320. In particular embodiments, cross entropy is employed as the loss function.

In various embodiments, the localization ground truth 570 is an image of one or more cells. In various embodiments, the localization ground truth 570 may be the same image as pluripotency ground truth 520 shown in FIG. 5A and further includes bounding structures. In various embodiments, the localization ground truth 570 represents the training image 555 that has undergone analysis for identifying locations of one or more cells in the training image 555. As one example, the locations of one or more cells in the training image 555 may be manually identified and bounding structures can be generated around the cells according to their manually identified locations.

In various embodiments, the localization ground truth 570 and the training image 555 represent paired images captured from a single sample. For example, the training image 555 is a first image captured from the single sample, and the localization ground truth 570 is a second image captured from the single sample, wherein locations of the cells are identifiable in the localization ground truth 570. In particular embodiments, the localization ground truth 570 is an immunocytochemistry image. In particular embodiments, the localization ground truth 570 is an immunofluorescent image. For example, the localization ground truth 570 is an immunocytochemistry or immunofluorescent image in which cell nuclei have been stained (e.g., 4',6-diamidino-2-phenylindole (DAPI)-stained). Here, the locations of one or more cells in the localization ground truth 570 may be identified using a nuclei segmentation algorithm that determines the locations of cell nuclei according to the cell nuclei stain, which serve as a proxy for locations of corresponding cells.

In various embodiments, the pluripotency model 310 and the cell localization model 320 are separately trained. In various embodiments, the pluripotency model 310 and the cell localization model 320 are jointly trained. Thus, the parameters of the pluripotency model 310 and the parameters of the cell localization model 320 can be iteratively adjusted together across training examples.

Isolating Cells According to Pluripotency Metrics

Disclosed herein are methods for isolating cells from a population of cells according to pluripotency metrics that are determined for the population of cells. In various embodiments, one or more pluripotent cells (e.g., pluripotent cells based on the determined pluripotency metrics assigned to those cells) are isolated from non-pluripotent cells (e.g., non-pluripotent cells based on determined pluripotency metrics assigned to those cells). In various embodiments, pluripotent cells can be isolated and then cultured to enable subsequent manipulation of these pluripotent cells. In some embodiments, non-pluripotent cells are desirable. Therefore, one or more non-pluripotent cells (e.g., non-pluripotent cells based on the determined pluripotency metrics assigned to those cells) are isolated from pluripotent cells (e.g., pluripotent cells based on determined pluripotency metrics assigned to those cells). Thus, non-pluripotent cells can be isolated and then cultured to enable subsequent manipulation of these non-pluripotent cells. As an example, non-pluripotent cells can be used as training data for training the pluripotency model.

In various embodiments, isolating cells (e.g., pluripotent or non-pluripotent cells) involves performing a physical isolation. In various embodiments, the physical isolation of the cells is an automated process. As one example, the physical isolation includes physically removing and replating cells, thereby enabling subsequent manipulation of these cells. In one scenario, if pluripotent cells are desirable, physical isolation involves physically removing and replating pluripotent cells. In another scenario, if non-pluripotent cells are desirable, physical isolation involves physically removing and replating non-pluripotent cells.

As another example, the physical isolation includes physically removing one type of cells from the cell culture, thereby leaving behind the other type of cells. In one scenario, physical isolation includes physically removing non-pluripotent cells, thereby leaving behind pluripotent cells. Thus, the remaining pluripotent cells can be subsequently manipulated. In another scenario, physical isolation includes physically removing pluripotent cells, thereby leaving behind non-pluripotent cells. Here, the removed pluripotent cells can be replated and subsequently manipulated.

In various embodiments, isolating cells involves exposing the cells (e.g., pluripotent or non-pluripotent cells) to one or more reagents. In various embodiments, the reagents can include enzymes. In various embodiments, the reagents can be enzyme free. For example, an enzyme free reagent can include ReLeSR™ for disassociating cells, such as pluripotent and/or non-pluripotent cells.

In various embodiments, isolating cells involves exposing the other type of cells to an energy source, thereby eliminating the other type of cells. In one scenario, if pluripotent cells are desirable, isolating cells involves exposing non-pluripotent cells to an energy source. In another scenario, if non-pluripotent cells are desirable, isolating cells involves exposing pluripotent cells to an energy source. In various embodiments, the energy source is a laser (e.g., high intensity light or an ultraviolet laser) that ablates or eliminates the cells exposed to the laser. Thus, the desired cells (e.g., desired pluripotent cells or desired non-pluripotent cells) remain and can be subsequently manipulated.

In various embodiments, the isolated cells can be provided a treatment and further evaluated (e.g., evaluated using the pluripotency model and cell localization model in accordance with FIG. 3) to determine whether the pluripotency of the isolated cells has changed in response to the treatment. Example treatments can include treatments that cause the isolated cells to differentiate down a particular cell lineage. Therefore, re-evaluating the cells can inform whether the isolated cells have successfully differentiated down the desired cell lineage. For example, isolated cells can be re-evaluated to determine whether the cells have differentiated down any of ectoderm, endoderm, or mesoderm lineages.

Computing Device

The methods described above, including the methods of characterizing pluripotency of cells, are, in some embodiments, performed on a computing device. Examples of a computing device can include a personal computer, desktop computer laptop, server computer, a computing node within a cluster, message processors, hand-held devices, multi-processor systems, microprocessor-based or programmable consumer electronics, network PCs, minicomputers, mainframe computers, mobile telephones, PDAs, tablets, pagers, routers, switches, and the like.

Figure 6:
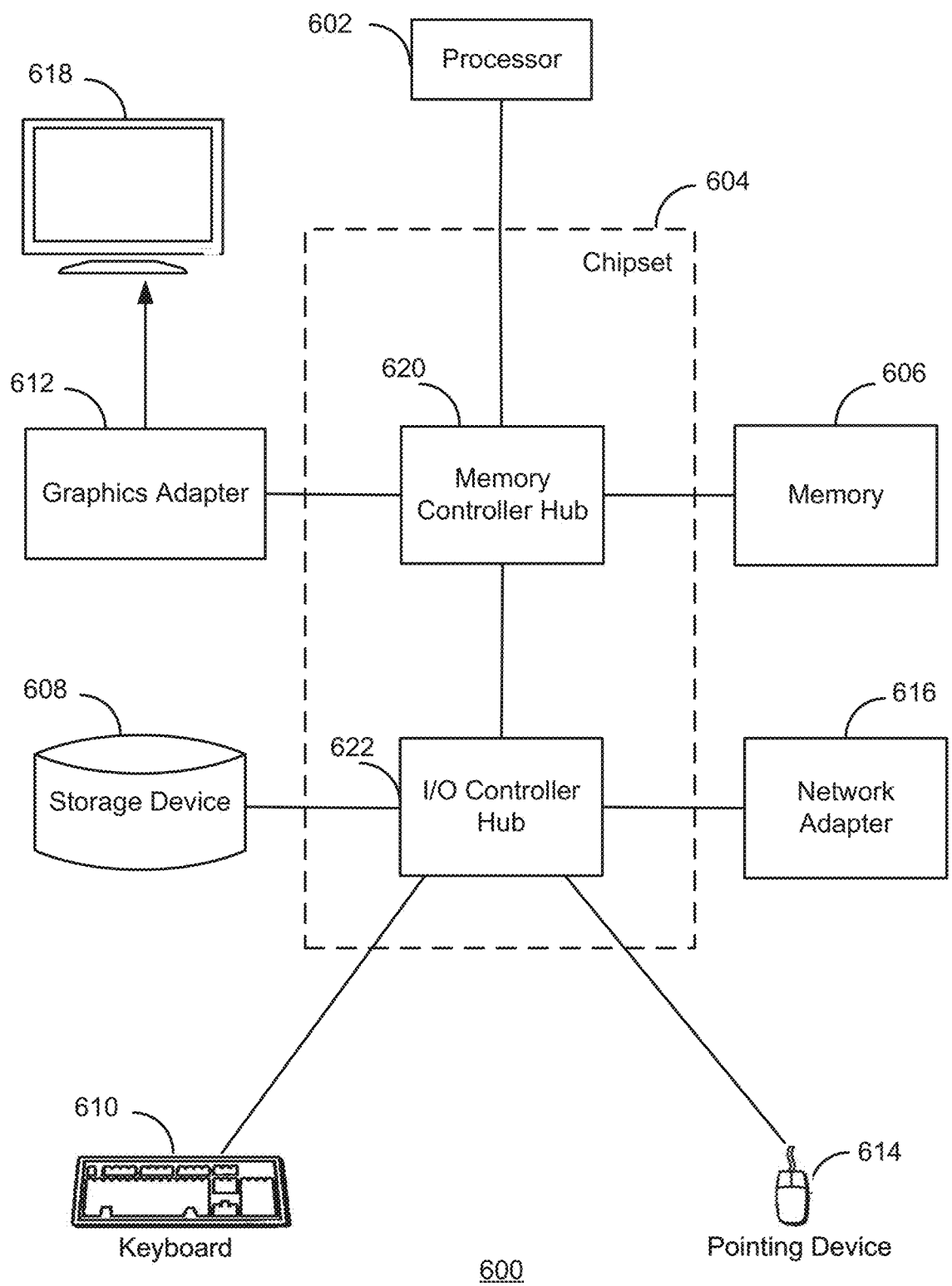
FIG. 6 illustrates an example computing device for implementing system and methods described in FIGS. 1-5B.

FIG. 6 illustrates an example computing device for implementing system and methods described in FIGS. 1-5B. In some embodiments, the computing device 600 includes at least one processor 602 coupled to a chipset 604. The chipset 604 includes a memory controller hub 620 and an input/output (I/O) controller hub 622. A memory 606 and a graphics adapter 612 are coupled to the memory controller hub 620, and a display 618 is coupled to the graphics adapter 612. A storage device 608, an input interface 614, and network adapter 616 are coupled to the I/O controller hub 622. Other embodiments of the computing device 600 have different architectures.

The storage device 608 is a non-transitory computer-readable storage medium such as a hard drive, compact disk read-only memory (CD-ROM), DVD, or a solid-state memory device. The memory 606 holds instructions and data used by the processor 602. The input interface 614 is a touch-screen interface, a mouse, track ball, or other type of input interface, a keyboard, or some combination thereof, and is used to input data into the computing device 600. In some embodiments, the computing device 600 may be configured to receive input (e.g., commands) from the input interface 614 via gestures from the user. The graphics adapter 612 displays images and other information on the display 618. For example, the display 618 can show characterizations of pluripotency of cells. In various embodiments, the display 618 can show characterizations of pluripotency of cells on an image including the cells. For example, for one or more cells positioned at various locations in the image, the display 618 can display the predicted pluripotency of the one or more cells at the various locations in the image. Therefore, a viewer of the display 618 can readily understand the predicted pluripotency of any of the one or more cells that are positioned at various locations in the image.

The network adapter 616 couples the computing device 600 to one or more computer networks. The computing device 600 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 608, loaded into the memory 606, and executed by the processor 602.

The types of computing devices 600 can vary from the embodiments described herein. For example, the computing device 600 can lack some of the components described above, such as graphics adapters 612, input interface 614, and displays 618. In some embodiments, a computing device 600 can include a processor 602 for executing instructions stored on a memory 606.

The training and deployment of a predictive model (e.g., one or both of the pluripotency model and cell localization model) can be implemented in hardware or software, or a combination of both. In one embodiment, a computer readable medium comprising computer executable instructions configured to implement any of the methods described herein can be implemented. In various embodiments, the computer readable medium is a non-transitory computer readable medium. In some embodiments, the computer readable medium is a part of a computer system (e.g., a memory of a computer system). The non-transitory machine-readable storage medium, such as one described above, is provided, the medium comprising a data storage material encoded with machine readable data which, when using a machine programmed with instructions for using said data, is capable of implementing a predictive model for characterizing pluripotency of cells.

Embodiments of the methods described above can be implemented in computer programs executing on programmable computers, comprising a processor, a data storage system (including volatile and non-volatile memory and/or storage elements), a graphics adapter, an input interface, a network adapter, at least one input device, and at least one output device. A display is coupled to the graphics adapter.

Program code is applied to input data to perform the functions described above and generate output information. The output information is applied to one or more output devices, in known fashion. The computer can be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

System Environment

Figure 7A:
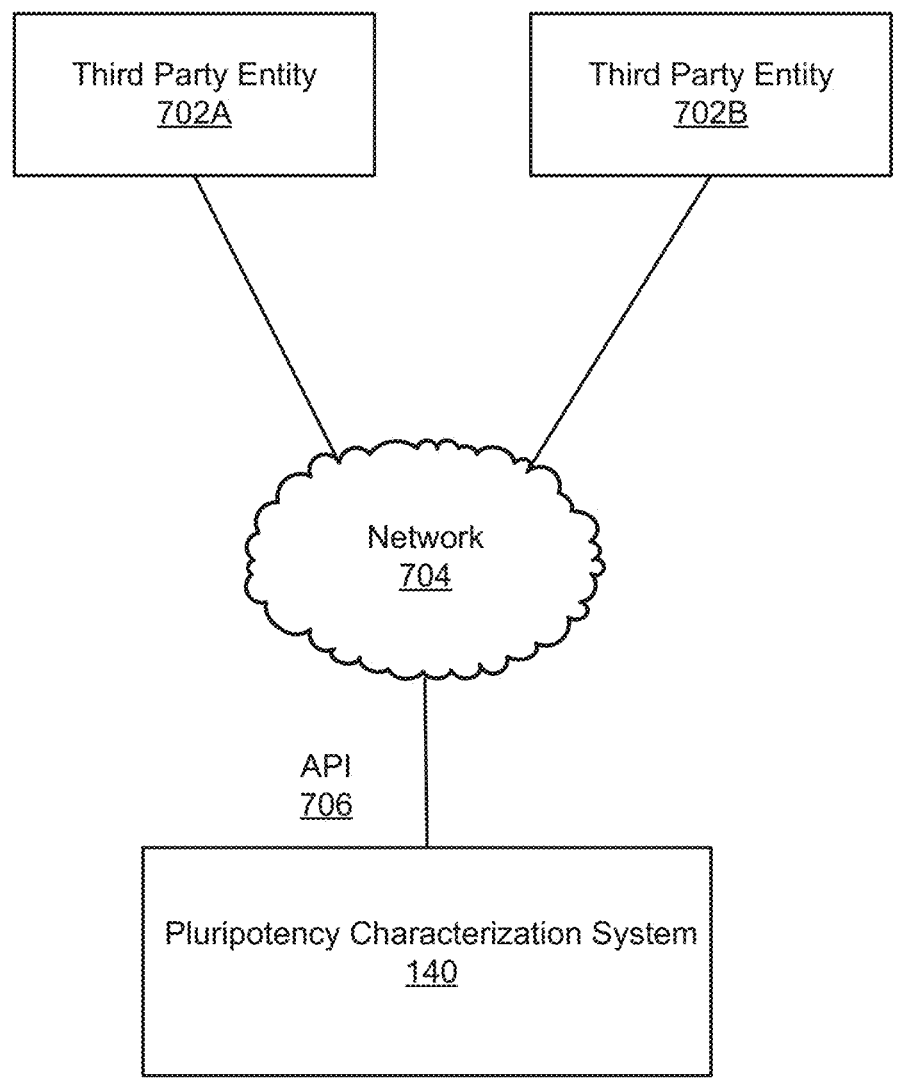
FIG. 7A depicts an overall system environment involving the pluripotency characterization system, in accordance with an embodiment.

FIG. 7A depicts an overall system environment involving the pluripotency characterization system, in accordance with an embodiment. The overall system environment 700 includes a pluripotency characterization system 140, as described earlier in reference to FIGS. 1 and 2, and one or more third party entities 702A and 702B in communication with one another through a network 704. FIG. 7A depicts one embodiment of the overall system environment 700. In other embodiments, additional or fewer third party entities 702 in communication with the pluripotency characterization system 140 can be included. Generally, the pluripotency characterization system 140 implements predictive models that characterize pluripotency of cells based on one or more images of the cells. The third party entities 702 communicate with the pluripotency characterization system 140 for purposes associated with implementing the predictive models or obtaining predictions or results from the predictive models.

Figure 7B:
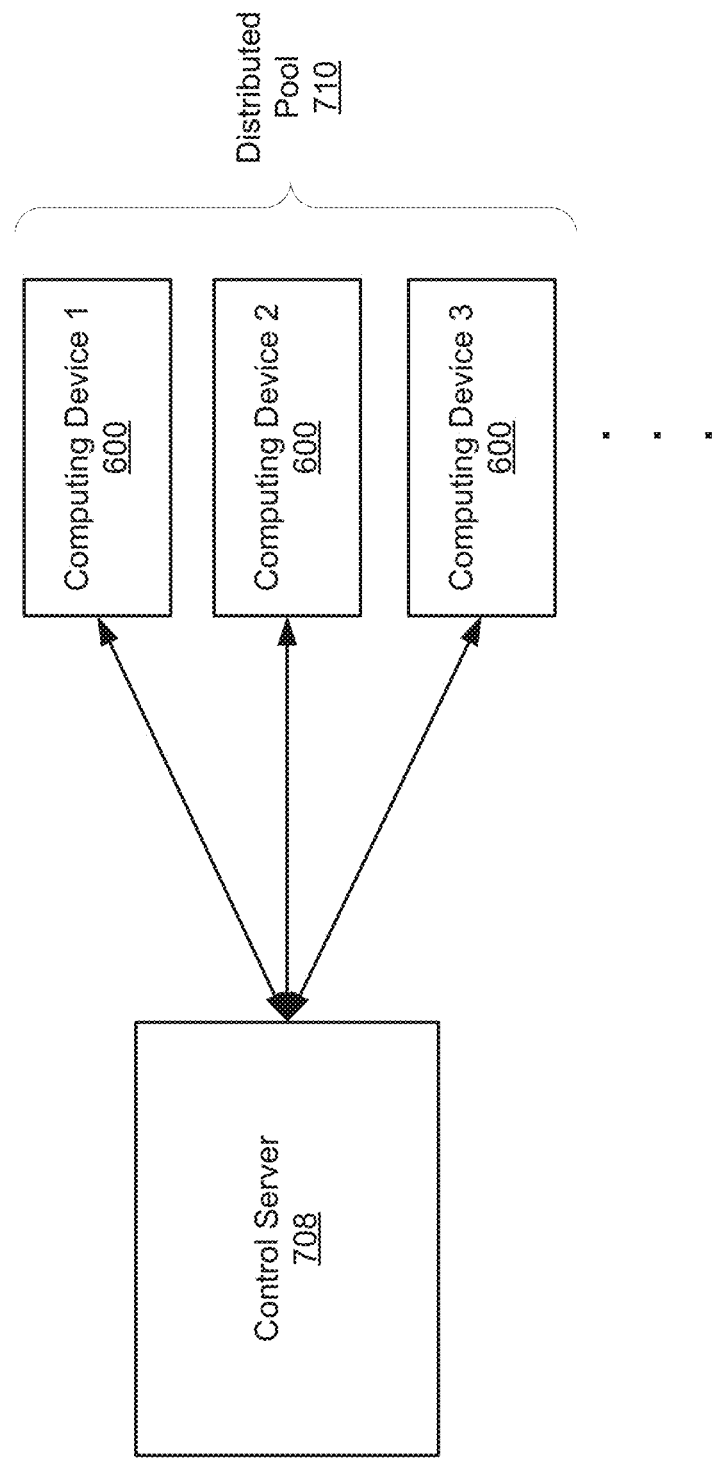
FIG. 7B is an example depiction of a distributed computing system environment for implementing the system environment of FIG. 7A and methods described above, such as the methods described in FIGS. 1-5B.

In various embodiments, the different entities depicted in FIGS. 7A and/or FIG. 7B may implement one or more computing devices to perform the methods described above, including the methods of training and/or deploying a predictive model for characterizing pluripotency of cells. For example, the pluripotency characterization system 140, third party entity 702A, and third party entity 702B may each employ one or more computing devices.

Third Party Entity

In various embodiments, the third party entity 702 represents a partner entity of the pluripotency characterization system 140 that operates either upstream or downstream of the pluripotency characterization system 140. As one example, the third party entity 702 operates upstream of the pluripotency characterization system 140 and provide information to the pluripotency characterization system 140 to enable the development and/or deployment of the predictive model. In various embodiments, a third party entity 702A or 702B can capture images of cells and provide the captured images to the pluripotency characterization system 140 for analysis using a predictive model. In various embodiments, a third party entity 702A or 702B can train a predictive model using training images and thereafter, can provide the trained predictive model to the pluripotency characterization system 140. The pluripotency characterization system 140 analyzes the captured images using the predictive model characterize pluripotency of cells in the images. As another example, the third party entity 702 operates downstream of the pluripotency characterization system 140. In this scenario, the pluripotency characterization system 140 characterizes the pluripotency of cells and then provides information comprising the pluripotency of cells to the third party entity 702. For example, the pluripotency characterization system 140 can serve as a provider that analyzes images of cells cultured by a third party entity 702 and then provides predicted pluripotency of the cells back to the third party entity 702. The third party entity 702 can subsequently use the predicted pluripotency of cells for their own purposes. For example, the third party entity 702 may isolate the cells that are predicted to be pluripotent and discard cells that are not pluripotent. Thus, the third party entity 702 may perform experiments on the isolated, pluripotent cells.

Network

This disclosure contemplates any suitable network 704 that enables connection between the pluripotency characterization system 140 and third party entities 702. The network 704 may comprise any combination of local area and/or wide area networks, using both wired and/or wireless communication systems. In one embodiment, the network 704 uses standard communications technologies and/or protocols. For example, the network 704 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 704 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 704 may be represented using any suitable format, such as hypertext markup language (HTML) or extensible markup language (XML). In some embodiments, all or some of the communication links of the network 704 may be encrypted using any suitable technique or techniques.

Application Programming Interface (API)

In various embodiments, the pluripotency characterization system 140 communicates with third party entities 702A or 702B through one or more application programming interfaces (API) 706. The API 706 may define the data fields, calling protocols and functionality exchanges between computing systems maintained by third party entities 702 and the pluripotency characterization system 140. The API 706 may be implemented to define or control the parameters for data to be received or provided by a third party entity 702 and data to be received or provided by the pluripotency characterization system 140. The API 706 may support implementation of licensing restrictions and tracking mechanisms for information provided by the pluripotency characterization system 140 to a third party entity 702. Such licensing restrictions and tracking mechanisms supported by API 706 may be implemented using blockchain-based networks, secure ledgers and information management keys. Examples of APIs include remote APIs, web APIs, operating system APIs, or software application APIs.

An API may be provided in the form of a library that includes specifications for routines, data structures, object classes, and variables. In other cases, an API may be provided as a specification of remote calls exposed to the API consumers. An API specification may take many forms, including an international standard such as POSIX, vendor documentation such as the Microsoft Windows API, or the libraries of a programming language, e.g., Standard Template Library in C++ or Java API. In various embodiments, the pluripotency characterization system 140 includes a set of custom API that is developed specifically for the pluripotency characterization system 140.

Distributed Computing Environment

In some embodiments, the methods described above, including the methods of training and deploying a pluripotency model and/or cellular localization model, are, performed in distributed computing system environments where local and remote computer systems, which are linked (either by hardwired data links, wireless data links, or by a combination of hardwired and wireless data links) through a network, both perform tasks. In some embodiments, one or more processors for implementing the methods described above may be located in a single geographic location (e.g., within a home environment, an office environment, or a server farm). In various embodiments, one or more processors for implementing the methods described above may be distributed across a number of geographic locations. In a distributed computing system environment, program modules may be located in both local and remote memory storage devices.

FIG. 7B is an example depiction of a distributed computing system environment for implementing the system environment of FIG. 7A and methods described above, such as the methods described in FIGS. 1-5B. The distributed computing system environment 750 can include a control server 708 connected via communications network with at least one distributed pool 710 of computing resources, such as computing devices 600, examples of which are described above in reference to FIG. 6. In various embodiments, additional distributed pools 710 may exist in conjunction with the control server 708 within the distributed computing system environment 750. Computing resources can be dedicated for the exclusive use in the distributed pool 710 or shared with other pools within the distributed processing system and with other applications outside of the distributed processing system. Furthermore, the computing resources in distributed pool 710 can be allocated dynamically, with computing devices 600 added or removed from the pool 710 as necessary.

In various embodiments, the control server 708 is a software application that provides the control and monitoring of the computing devices 600 in the distributed pool 710. The control server 708 itself may be implemented on a computing device (e.g., computing device 600 described above in reference to FIG. 6). Communications between the control server 708 and computing devices 600 in the distributed pool 710 can be facilitated through an application programming interface (API), such as a Web services API. In some embodiments, the control server 708 provides users with administration and computing resource management functions for controlling the distributed pool 710 (e.g., defining resource availability, submission, monitoring and control of tasks to performed by the computing devices 600, control timing of tasks to be completed, ranking task priorities, or storage/transmission of data resulting from completed tasks).

In various embodiments, the control server 708 identifies a computing task to be executed across the distributed computing system environment 750. The computing task can be divided into multiple work units that can be executed by the different computing devices 600 in the distributed pool 710. By dividing up and executing the computing task across the computing devices 600, the computing task can be effectively executed in parallel. This enables the completion of the task with increased performance (e.g., faster, less consumption of resources) in comparison to a non-distributed computing system environment.

In various embodiments, the computing devices 600 in the distributed pool 710 can be differently configured in order to ensure effective performance for their respective jobs. For example, a first set of computing devices 600 may be dedicated to performing collection and/or analysis of phenotypic assay data. A second set of computing devices 600 may be dedicated to performing the training of the pluripotency model and/or the cell localization model. The first set of computing devices 600 may have less random access memory (RAM) and/or processors than the second set of second computing devices 600 given the likely need for more resources when training or deploying the pluripotency model and/or the cell localization model.

The computing devices 600 in the distributed pool 710 can perform, in parallel, each of their jobs and when completed, can store the results in a persistent storage and/or transmit the results back to the control server 708. The control server 105 can compile the results or, if needed, redistribute the results to the respective computing devices 600 to for continued processing.

In some embodiments, the distributed computing system environment 750 is implemented in a cloud computing environment. In this description, "cloud computing" is defined as a model for enabling on-demand network access to a shared set of configurable computing resources. For example, the control server 708 and the computing devices 600 of the distributed pool 710 may communicate through the cloud. Thus, in some embodiments, the control server 708 and computing devices 600 are located in geographically different locations. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

EXAMPLES

Example 1: Predictive Models for Predicting Cellular Pluripotency

Disclosed herein is a method to determine pluripotency status of induced pluripotent stem cells (iPSCs) in culture through live cell bright field microscopy. In this example, the method used a deep learning model to translate an input bright field image to a pluripotency mask and generate cell localizations. The model output was the location of each cell in the image along with its pluripotency status.

A deep learning model was trained with paired brightfield and immunofluorescent imaging for Nanog expression. Specifically, the training data were generated from experiments with controlled differentiations of iPSCs into various lineages, where the cells were fixed and stained with DAPI and Nanog at various time points, and subsequently imaged in brightfield and fluorescent channels. The deep learning model was used to generate a transformation from the brightfield image to the Nanog target image. Original images of cells acquired at the field of view level of 1992×1992 resolution were randomly sampled to generate tiles with a resolution of 256×256. The brightfield image was normalized at the tile level through z-scoring. The architecture of the model took, as input, a z-scored transformed brightfield image, and passed that image through several levels of nonlinear transformation layers with decreasing spatial resolution. The model up-sampled the result to the spatial resolution of the target image. The architecture also included skip layers from the high resolution downsampling layer to the upsampling layers to enable learning of local features. An example of the model architecture is described above in reference to FIG. 4. The output of the model was an image (e.g., intermediate mask representation) of the same spatial resolution as the input where each pixel was a prediction of the Nanog expression at the corresponding pixel in the input image.

In order to maintain information on Nanog expression across tiles, the immunofluorescent image cannot be normalized in the same way as the brightfield image. Instead the raw intensity values of the immunofluorescent images were divided by a constant (global max value for unsigned 16-bit integer). The purpose of this was to reduce the magnitude of the intensity values to be less than 1 but to preserve the relative intensity differences across various experimental conditions. Converting the predicted values back to the immunofluorescence intensity domain included multiplying the resulting value by the same constant. Iterations of stochastic gradient descent were run on batches of the training set with Adam as the optimization algorithm and cross entropy as the loss function until convergence. The training was completed on a single GPU machine.

There were two parts to the deep learning model that made up the method: the pluripotency model and the cell localization model. The pluripotency model generated a real valued intensity mask (e.g., intermediate mask representation) that approximated the Nanog readout from the immuno-fluorescent ground truth image. The cell detection model generated bounding box localizations that provided the locations of each cell in the image. The predicted intermediate mask representation along with the cell localizations were used to calculate the aggregate metric for the input bright field image of the field of view. The aggregate readout was calculated as the percentage of cells in the image that were pluripotent.

Figure 8:
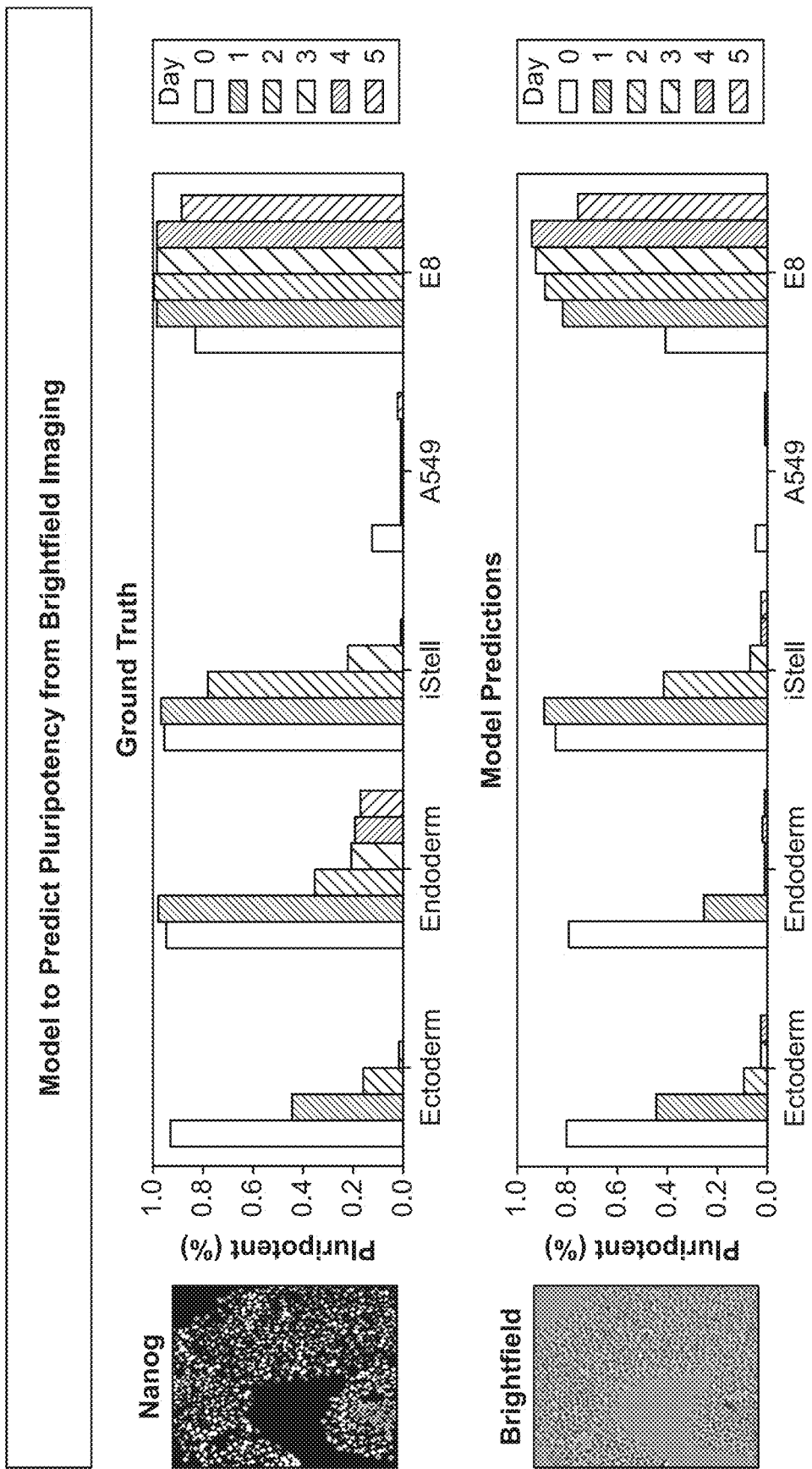
FIG. 8 shows the example performance of a predictive model for predicting pluripotency of cells included in images.

FIG. 8 shows the example performance of a predictive model for predicting pluripotency of cells included in images. The cells included cells derived from the ectoderm layer, cells derived from the endoderm layer, cells derived from the mesoderm layer (e.g., iPSC derived hepatic stellate (iStell) cells) as well terminally differentiated cells (e.g., A549 cells). Specifically, A549 cells, as a terminally differentiated cell line, served as a negative control. Additionally, E8 refers to induced pluripotent stem cells (iPSC) media and therefore, served as a positive control.

Of note, the predictive model was deployed on brightfield images captured from cells over successive days (e.g., 5 days) to predict the change in pluripotency of the cells. Predictions of pluripotency of cells from the model were compared to reference ground truths of cellular pluripotency represented by Nanog immunofluorescent images captured from the same cells. Specifically, the top panel of FIG. 8 shows an example Nanog immunofluorescent image as well as measures of pluripotency of the five different types of cells from Day 0 to Day 5. The bottom panel of FIG. 8 shows an example bright field image that was analyzed by the predictive model. Furthermore, the bottom panel of FIG. 8 shows the predictions of pluripotency of the five different types of cells from Day 0 to Day 5. Generally, the pluripotency predictions align with the reference ground truth, demonstrating that the prediction model was able to predict cellular pluripotency using bright-field images of cells.

Furthermore, a cell based pluripotency metric was generated to evaluate the similarity of the predicted mask to the target values for the purposes of interpretability and robustness. Specifically for each cell in the image the ground truth and predicted pluripotency label was determined for that cell. This enables analysis of the overall trends in pluripotency across experimental conditions and further enables generating metrics of prediction performance on a cellular level. The first step of this process was to determine the spatial localization of the cells in the image. Using a nuclei segmentation algorithm on the DAPI channel (immunofluorescent channel that lights up DNA in the nucleus) the locations of individual cellular nuclei were determined, which were used as a proxy for the location of the cell. For each location, a bounding box was generated around the nuclei. The ground truth Nanog immunofluorescence image and predicted image were transformed into binary images by thresholding the values by a constant, determined empirically by graphing the intensity distributions of the positive and negative control groups. The portion of the pixels in each bounding box that were positive based on the binary images was calculated. A cutoff (0.5) was applied to determine the pluripotency label for the given cell. With a ground truth label and predicted label from each cell, the change in the pluripotency along different experimental conditions can be tracked. Classification metrics on the labels such as accuracy, precision, and recall were calculated. Here, the model performance was as follows: 1) Accuracy=0.91, 2) Precision=0.94, and 3) Recall=0.75.

Example 2: Predictive Models for Predicting Cellular Pluripotency Using Protein Markers A deep learning model is trained with paired brightfield and immunofluorescent imaging for protein marker expression that is correlated with cellular pluripotency. Here, protein marker expression correlated with cellular pluripotency includes any of Oct4, Sox2, Klf4, c-Myc, Nanog, Lin28, SSEA-4, Tra-1-60, Tra-1-81, Alkaline Phosphatase, CD9, E-cadherin, and PODXL.

Specifically, training data are generated from experiments with controlled differentiations of iPSCs into various lineages, where the cells are fixed and stained with protein markers at various time points, and subsequently imaged in brightfield and fluorescent channels. For example, cells are fixed and stained with Oct4 at various time points and subsequently imaged in brightfield and fluorescent channels. As another example, cells are fixed and stained with Sox2 at various time points and subsequently imaged in brightfield and fluorescent channels. Additional examples include fixing cells and staining with any of Klf4, c-Myc, Lin28, SSEA-4, Tra-1-60, Tra-1-81, Alkaline Phosphatase, CD9, E-cadherin, and PODXL. These cells are imaged in brightfield and fluorescent channels.

The deep learning model is used to generate a transformation from the brightfield image to the target image (e.g., target image with stained protein biomarkers indicative of pluripotency, including a target image with stained biomarkers including e.g., Oct4, Sox2). The architecture of the model takes, as input, a transformed brightfield image, and passes that transformed brightfield image through several levels of nonlinear transformation layers with decreasing spatial resolution. The model up-samples the result to the spatial resolution of the target image. The architecture also includes skip layers from the high resolution downsampling layer to the upsampling layers to enable learning of local features. An example of the model architecture is described above in reference to FIG. 4. The output of the model is an image (e.g., intermediate mask representation) of the same spatial resolution as the input where each pixel is a prediction of the protein biomarker expression at the corresponding pixel in the input image.

There are two parts to the deep learning model: the pluripotency model and the cell localization model. The pluripotency model generates a real valued intensity mask (e.g., intermediate mask representation) that approximates the protein biomarker readout (e.g., readout corresponding to any of Oct4, Sox2, Klf4, c-Myc, Nanog, Lin28, SSEA-4, Tra-1-60, Tra-1-81, Alkaline Phosphatase, CD9, E-cadherin, and PODXL) from the immuno-fluorescent ground truth image. The cell detection model generates bounding box localizations that provide the locations of each cell in the image. The intermediate mask representation along with the cell localizations are used to calculate the aggregate metric for the input bright field image of the field of view. The aggregate readout is calculated as the percentage of cells in the image that are pluripotent.

The predictive model is implemented for predicting pluripotency of various cells included in images including e.g., cells derived from the ectoderm layer, cells derived from the endoderm layer, cells derived from the mesoderm layer (e.g., iPSC derived hepatic stellate (iStell) cells) as well terminally differentiated cells (e.g., A549 cells).

The predictive model is deployed on brightfield images captured from cells over successive days to predict the change in pluripotency of the cells. Predictions of pluripotency of cells from the model are compared to reference ground truths of cellular pluripotency represented by protein biomarker immunofluorescent images captured from the same cells.

Altogether, immunofluorescence antibody based staining of protein markers of pluripotency, including pluripotency markers OCT4 and SOX2, are paired with brightfield images. These pluripotency markers are located in the nucleus and have similar expression profiles as Nanog in iPSCs. Therefore, pluripotency markers, such as OCT4 and SOX2, provide a similar level of concordance with the predictive model's predictions of pluripotency in iPSCs, including similar or better measurements in accuracy, precision, and recall as detailed in Example 1.

Example 3: Predictive Models for Predicting Cellular Pluripotency Using RNA-Fluorescence In Situ Hybridization (FISH)

A deep learning model is trained with paired brightfield and fluorescent images captured via RNA-FISH including mRNA expression that is correlated with cellular pluripotency. RNA-FISH is a method to detect and localize messenger ribonucleic acid (mRNA) within the cellular context without the need to remove the cell from the surface it is growing to isolate the mRNA. Here, mRNA expression from genes involved with pluripotency (e.g., any of Oct4, Sox2, Klf4, c-Myc, Nanog, Lin28, SSEA-4, Tra-1-60, Tra-1-81, Alkaline Phosphatase, CD9, E-cadherin, and PODXL) are identified, imaged, and paired with brightfield image for training the deep learning model.

Specifically, training data are generated from experiments with controlled differentiations of iPSCs into various lineages, where the cells undergo RNA-FISH for detecting mRNA expression of one or more pluripotent genes, and are imaged in brightfield and fluorescent channels. For example, cells undergo RNA-FISH for detecting Nanog mRNA expression at various time points and are imaged in brightfield and fluorescent channels. As another example, cells undergo RNA-FISH for detecting Oct4 mRNA expression at various time points and imaged in brightfield and fluorescent channels. As another example, cells undergo RNA-FISH for detecting Sox2 mRNA expression at various time points and are imaged in brightfield and fluorescent channels.

The deep learning model is used to generate a transformation from the brightfield image to the target fluorescent image (e.g., target image capturing mRNA expression of pluripotent genes via RNA-FISH). The architecture of the model takes, as input, a transformed brightfield image, and passes that transformed brightfield image through several levels of nonlinear transformation layers with decreasing spatial resolution. The model up-samples the result to the spatial resolution of the target image. The architecture also includes skip layers from the high resolution downsampling layer to the upsampling layers to enable learning of local features. An example of the model architecture is described above in reference to FIG. 4. The output of the model is an image (e.g., intermediate mask representation) of the same spatial resolution as the input where each pixel is a prediction of the mRNA expression (e.g., mRNA expression of a pluripotent gene) at the corresponding pixel in the input image.

There are two parts to the deep learning model: the pluripotency model and the cell localization model. The pluripotency model generates a real valued intensity mask (e.g., intermediate mask representation) that approximates the mRNA expression readout (e.g., readout corresponding to mRNA expression of any of Oct4, Sox2, Klf4, c-Myc, Nanog, Lin28, SSEA-4, Tra-1-60, Tra-1-81, Alkaline Phosphatase, CD9, E-cadherin, and PODXL). The cell detection model generates bounding box localizations that provide the locations of each cell in the image. The intermediate mask representation along with the cell localizations are used to calculate the aggregate metric for the input bright field image of the field of view. The aggregate readout is calculated as the percentage of cells in the image that are pluripotent.

The predictive model is implemented for predicting pluripotency of various cells included in images including e.g., cells derived from the ectoderm layer, cells derived from the endoderm layer, cells derived from the mesoderm layer (e.g., iPSC derived hepatic stellate (iStell) cells) as well terminally differentiated cells (e.g., A549 cells).

The predictive model is deployed on brightfield images captured from cells over successive days to predict the change in pluripotency of the cells. Predictions of pluripotency of cells from the model are compared to reference ground truths of cellular pluripotency represented by images of mRNA expression of pluripotent genes captured via RNA-FISH from the same cells.

Altogether, pairing images of mRNA expression of pluripotent genes captured via RNA-FISH with brightfield images provide a similar level of concordance with the model's predictions of pluripotency in iPSCs, but not in cells that are differentiating, including similar or better measurements in accuracy, precision, and recall as seen in Example 1.

Example 4: Predictive Models for Predicting Cellular Pluripotency Using Sequential Fluorescence In Situ Hybridization (SeqFISH+)

A deep learning model is trained with paired brightfield and fluorescent images captured via SeqFISH+ including mRNA expression of one or more genes that are correlated with cellular pluripotency. SeqFISH+ represents a modification of spatial transcriptomics, which is a process that allows visualization and quantitative analysis of the transcriptome with spatial resolution of an individual cell. SeqFISH+ enables the interrogation of mRNA expression for a large number of genes. For example, different fluorescent probes can be designed for hybridizing with different target mRNA sequences. Thus, using the different fluorescent probes through a sequential hybridization, strip wash, and hybridization process, SeqFISH+ enables the capture of images of mRNA expression of a large number of genes involved with pluripotency (e.g., any or all of Oct4, Sox2, Klf4, c-Myc, Nanog, Lin28, SSEA-4, Tra-1-60, Tra-1-81, Alkaline Phosphatase, CD9, E-cadherin, and PODXL).

Specifically, training data are generated from experiments with controlled differentiations of iPSCs into various lineages, where the cells undergo SeqFISH+ for detecting mRNA expression of one or more pluripotent genes, and are imaged in brightfield and fluorescent channels. For example, cells undergo SeqFISH+ for detecting Nanog mRNA expression at various time points and are imaged in brightfield and fluorescent channels. As another example, cells undergo SeqFISH+ for detecting Oct4 mRNA expression at various time points and imaged in brightfield and fluorescent channels. As another example, cells undergo SeqFISH+ for detecting Sox2 mRNA expression at various time points and are imaged in brightfield and fluorescent channels.

The deep learning model is used to generate a transformation from the brightfield image to the target fluorescent image (e.g., target image capturing mRNA expression of pluripotent genes via SeqFISH+). The architecture of the model takes, as input, a transformed brightfield image, and passes that transformed brightfield image through several levels of nonlinear transformation layers with decreasing spatial resolution. The model up-samples the result to the spatial resolution of the target image. The architecture also includes skip layers from the high resolution downsampling layer to the upsampling layers to enable learning of local features. An example of the model architecture is described above in reference to FIG. 4. The output of the model is an image (e.g., intermediate mask representation) of the same spatial resolution as the input where each pixel is a prediction of the mRNA expression (e.g., mRNA expression of a pluripotent gene) at the corresponding pixel in the input image.

There are two parts to the deep learning model: the pluripotency model and the cell localization model. The pluripotency model generates a real valued intensity mask (e.g., intermediate mask representation) that approximates the mRNA expression readout (e.g., readout corresponding to mRNA expression of one or more of Oct4, Sox2, Klf4, c-Myc, Nanog, Lin28, SSEA-4, Tra-1-60, Tra-1-81, Alkaline Phosphatase, CD9, E-cadherin, and PODXL). The cell detection model generates bounding box localizations that provide the locations of each cell in the image. The intermediate mask representation along with the cell localizations are used to calculate the aggregate metric for the input bright field image of the field of view. The aggregate readout is calculated as the percentage of cells in the image that are pluripotent.

The predictive model is implemented for predicting pluripotency of various cells included in images including e.g., cells derived from the ectoderm layer, cells derived from the endoderm layer, cells derived from the mesoderm layer (e.g., iPSC derived hepatic stellate (iStell) cells) as well terminally differentiated cells (e.g., A549 cells).

The predictive model is deployed on brightfield images captured from cells over successive days to predict the change in pluripotency of the cells. Predictions of pluripotency of cells from the model are compared to reference ground truths of cellular pluripotency represented by images of mRNA expression of pluripotent genes captured via SeqFISH+ from the same cells.

Altogether, pairing images of mRNA expression of pluripotent genes captured via SeqFISH+ with brightfield images provide a similar level of concordance with the model's predictions of pluripotency in iPSCs, but not in cells that are differentiating, including similar or better measurements in accuracy, precision, and recall as seen in Example 1.

The invention claimed is:

1. A method for characterizing pluripotency of a plurality of cells, the method comprising:
   obtaining a contrast image of the plurality of cells;
   applying, to the contrast image, a predictive model comprising a pluripotency model comprising one or more skip connections and a cell localization model, the pluripotency model configured to translate the contrast image to an intermediate mask representation comprising pluripotency predictions of biomarker intensities for the plurality of cells in the contrast image, and the cell localization model configured to identify locations of the plurality of cells within the contrast image; and
   generating at least pluripotency metrics for the plurality of cells according to the intermediate mask representation and using the identified locations of the plurality of cells predicted by the cell localization model, the pluripotency metrics indicative of pluripotency of the plurality of cells.

2. The method of claim 1 wherein the biomarker intensities comprise intensities of biomarkers selected from any of Oct4, Sox2, Klf4, c-Myc, Nanog, Lin28, SSEA-4, Tra-1-60, Tra-1-81, Alkaline Phosphatase, CD9, E-cadherin, and PODXL.

3. The method of claim 1, wherein the predictive model is trained using one or more images indicative of expression profiles of one or more genes correlated to cellular pluripotency determined via RNA fluorescent in situ hybridization (RNA-FISH) or sequential fluorescence in situ hybridization (SeqFISH+).

4. The method of claim 1, wherein the intermediate mask representation shares a same image resolution as the contrast image.

5. The method of claim 1, wherein the pluripotency model is a neural network.

6. The method of claim 1, wherein the pluripotency model is a convolutional neural network comprising downsampling operators and upsampling operators.

7. The method of claim 1, wherein the cell localization model is a neural network.

8. The method of claim 7, wherein the cell localization predictive model generates bounding box localizations for each cell of at least a subset of the plurality of cells.

9. The method of claim 8, wherein generating pluripotency metrics for the plurality of cells further comprises: for a cell at an identified location predicted by the cell localization model: determining a proportion of pixels in the intermediate mask representation at the identified location with a value that is indicative of the cell being pluripotent.

10. The method of claim 1, wherein the predictive model is trained with paired contrast images and immunofluorescent images.

11. The method of claim 1, wherein obtaining the contrast image of the plurality of cells comprises:
culturing the plurality of cells; and
capturing the contrast image of the plurality of cells.

12. The method of claim 11, wherein the plurality of cells are cultured in vitro or ex vivo.

13. The method of claim 1, wherein the plurality of cells are selected from any of induced pluripotent cells (iPSCs), embryonic stem cells, or cells derived from germ layers.

14. The method of claim 1, wherein the contrast image is any of a bright-field image, phase-contrast image, dark-field image, Reinberg Illumination image, or polarization image.

15. The method of claim 1, wherein the contrast image is captured using optical microscopy.

16. A method for characterizing pluripotency of a plurality of cells, the method comprising:
obtaining a contrast image of the plurality of cells;
applying a predictive model to the contrast image, the predictive model configured to translate the contrast image to an intermediate mask representation comprising pluripotency predictions for the plurality of cells in the contrast image, wherein the intermediate mask representation is a representation comprising pluripotency predictions according to sequencing data; and
generating pluripotency metrics for the plurality of cells according to the intermediate mask representation, the pluripotency metrics indicative of pluripotency of the plurality of cells.

17. The method of claim 16, wherein the sequencing data comprise RNA-seq sequencing data describing transcriptional sequencing profiles that are indicative of pluripotency.

18. The method of claim 16, wherein the sequencing data comprise DNA-seq sequencing data.

19. The method of claim 18, wherein the DNA-seq sequencing data comprise ATAC-seq sequencing data.

20. The method of claim 18, wherein the sequencing data comprise epigenetic signatures that are indicative of pluripotency.

21. The method of claim 20, wherein the epigenetic signatures comprise histone or DNA methylation statuses of a genome that are indicative of pluripotency.

22. The method of claim 16, further comprising:
identifying one or more cells from the plurality of cells based on the generated pluripotency metrics; and
isolating the identified one or more cells from the plurality of cells.

23. The method of claim 22, wherein isolating the one or more cells comprises ablating non-identified cells while maintaining the identified one or more cells.

24. The method of claim 22, wherein isolating the one or more cells comprises:
physically removing the isolated one or more cells from the plurality of cells; and culturing the physically removed isolated one or more cells.

* * * * *